US007566559B2

(12) United States Patent
Reinhard

(10) Patent No.: US 7,566,559 B2
(45) Date of Patent: Jul. 28, 2009

(54) HUMAN CYCLIN-DEPENDENT KINASE (HPNQALRE)

(75) Inventor: Christoph Reinhard, Alameda, CA (US)

(73) Assignee: Novartis Vaccines and Diagnostics, Inc., Emeryville, CA (US)

(*) Notice: Subject to any disclaimer, the term of this patent is extended or adjusted under 35 U.S.C. 154(b) by 0 days.

(21) Appl. No.: 11/774,306

(22) Filed: Jul. 6, 2007

(65) Prior Publication Data

US 2008/0050797 A1 Feb. 28, 2008

Related U.S. Application Data

(60) Division of application No. 10/663,896, filed on Sep. 16, 2003, now Pat. No. 7,250,256, which is a continuation of application No. 09/464,065, filed on Dec. 15, 1999, now abandoned.

(60) Provisional application No. 60/112,497, filed on Dec. 16, 1998.

(51) Int. Cl.
  *C12N 9/12* (2006.01)
  *C12N 9/00* (2006.01)
  *C12Q 1/00* (2006.01)
  *C12Q 1/68* (2006.01)
  *C07H 21/04* (2006.01)

(52) U.S. Cl. .............. 435/194; 435/4; 435/6; 435/183; 536/23.2

(58) Field of Classification Search ............ None
See application file for complete search history.

(56) References Cited

U.S. PATENT DOCUMENTS 5,968,800 A * 10/1999 Gerhold ............... 435/194
7,250,256 B2 * 7/2007 Reinhard .............. 435/6

FOREIGN PATENT DOCUMENTS

| WO | WO 96-28555 | 9/1996 |
| WO | WO 97-25345 | 7/1997 |
| WO | WO 98-35015 | 8/1998 |
| WO | WO 98-40483 | 9/1998 |

OTHER PUBLICATIONS

Chica et al. Curr Opin Biotechnol. Aug. 2005;16(4):378-84.*
Gerhold. Accession AAW49083. Dec. 7, 1998.*
Alignement of SEQ ID No. 3 of US Patent 5,968,800 (Gerhold) to SEQ ID No. 2 of application.*
Leibiger et al., *Short-Term Regulation of Insulin Gene Transcription by Glucose*, Proceedings of the Nat'l Academy of Sciences of USA, 95:9307-9312 (1998).
Lock et al., *Potentiation of Etoposide-Induced Apoptosis by Staurosporine in Human Tumor Cells is Associated with Events Downstream of DNA-Protein Complex Formation*, Cancer Chemother. Pharmocol, 39:399-409 (1997).
Morgan, *Cyclin-Dependent Kinases: Engines, Clocks, and Microprocessors*, Annu. Rev. Cell Dev. Biol., 13:261-291 (1997).
Accession No. AA065538 (1996), Marra, et al., *Mus musculus cDNA clone IMAGE:515877 5' similar to TR:G758205 G758205 CDC2PA Gene*.
Lew et al., *Regulatory Roles of Cyclin Dependent Kinase Phophorylation in Cell Cycle Control*, Curr. Opin. Cell Biol., 8:795-804 (1996).
Shuttleworth, *The Regulation and Function of cdk7*, Prog. Cell Cycle Res., 1:229-240 (1995).
Hopp et al., *A Computer Program for Predicting Protein Antigenic Determinants*, Mol. Immunol., 20(4):a483-489 (1983).
Sutcliffe et al., *Antibodies That React with Predetermined Sites on Proteins*, Science, 219:660-666 (1983).
Hopp et al., *Prediction of Protein Antigenic Determinants from Amino Acid Sequences*, Proc. Nat'l. Acad. Sci. USA, 78(6) 3824-3828 (1981).
Whisstock et al, Q Rev Biophys. 36(3):307-40 (Aug. 2003).
Molina et al., Tumour Biol. 26(6):281-293 (Oct. 25, 2005).
Database Biosis Biosciences Information Service, Philadelphia, PA, US: Oya M. et al., *Expression of G1fwdarwS transition regulatory molecules in human urothelial cancer*, pp. 1-2, (Jul. 1998).
Meikrantz W et al., Suppression of apoptosis by dominant negative mutants of cyclin-dependent protein kinases, *J. Biol. Chem.*, vol. 271, No. 17 pp. 10205-10209 (1996).
Liu, Y. et al., p42, a novel cyclin-dependent kinase-activating kinase in mammalian cells J. Biol. Chem. vol. 279, No. 6, pp. 4507-4514 (2004).
Alignment of CDK10 of D2 (WO-98/35015 filed Feb. 6, 1998) to Seq ID No. 4 of EP Application No. 99967389.0 filed Dec. 16, 1999, 1 page.
Alignment of HCEDH81 of D3 (WO-98/40483 filed Mar. 12, 1998) to Seq ID No. 4 of EP Application No. 99967389.0 filed Dec. 16, 1999, 1 page.
Alignment of SEQ ID No. 3 of U.S. Appl. No. 09/464,065, filed Dec. 15, 1999 (Reinhard) to GenBank Accession No. AA065538 last updated Feb. 3, 1997 ("Alignment 2"), 2 pages.
Alignment of SEQ ID No. 5 of U.S. Appl. No. 09/464,065, filed Dec. 15, 1999 (Reinhard) to GenBank Accession No. AA065538 last updated Feb. 3, 1997 ("Alignment 3"), 2 pages.
Alignment of SEQ ID No. 6 of U.S. Appl. No. 09/454,065, filed Dec. 15, 1999 (Reinhard) to GenBank Accession No. AA065538 last updated Feb. 3, 1997 ("Alignment 1"), 1 page.
Ciardiello, F. et al. (May 2001). "Inhibition of Growth Factor Production and Angiogenesis in Human Cancer Cells by ZD1839 (Iressa), a Selective Epidermal Growth Factor Receptor Tyrosine Kinase Inhibitor," *Clinical Cancer Research* 7:1459-1465.

(Continued)

*Primary Examiner*—Christian L Fronda
(74) *Attorney, Agent, or Firm*—Lisa Alexander; Patricia Tsao

(57) ABSTRACT

A human gene encoding a novel cyclin-dependent kinase termed hPNQALRE and its expression products can be used to provide reagents and methods for detecting neoplasia. Compositions and methods for treating proliferative disorders and neoplasia are also provided.

4 Claims, 4 Drawing Sheets

OTHER PUBLICATIONS

EMBL Accession No. AI386000, last updated Jan. 29, 1999, located at <http://srs.ebi.ac.uk/srsbin/cgi-bin/wgetz?-page+EntryPage+-id+1YUGI1Z7BNm+-e+[EMBL:AI386000]+-vn+2> visited on Jan. 23, 2009. (2 pages).

EMBL Accession No. P50613, last updated Oct. 1, 1996, located at <http://www.uniprot.org/uniprot/P50613.txt> visited on Jan. 23, 2009. (6 pages).

International Search Report mailed Sep. 18, 2000, for PCT Application No. PCT/US99/30113 filed Dec. 16, 1999, 6 pages.

Koeffler, H. P. et al. (Sep. 1980). "Human Myeloid Leukemia Cell Lines: A Review," *Blood* 56(3):344-350.

MacKeigan, J. P. et al. (Jun. 2005). "Sensitized RNAi Screen of Human Kinases and Phosphatases Identifies New Regulators of Apoptosis and Chemoresistance," *Nature Cell Biology* 7(6):591-600, Supplementary Information pp. 1-4.

Partial European Search Report and Written Opinion mailed Dec. 22, 2008, for EP Application No. 08006175.7 filed Dec. 16, 1999, 14 pages.

Partial European Search Report mailed Aug. 28, 2008, for EP Application No. 08006175.7 filed Dec. 16, 1999, 9 pages.

Wohlbold, L. et al. (Mar. 1, 2006). "The Cyclin-Dependent Kinase (CDK) Family Member PNQALRE/CCRK Supports Cell Proligeration but has No Intrinsic CDK-Activating Kinase (CAK) Activity," *Cell Cycle* 5(5):546-554.

\* cited by examiner

Clustal W(1.4) multiple sequence alignment

4 Sequences Aligned.          Alignment Score = 12736
Gaps Inserted = 4             Conserved Identities = 308

Pairwise Alignment Mode: Slow                                FIGURE 1
Pairwise Alignment Parameters:
    Open Gap Penalty = 10.0   Extend Gap Penalty = 0.1
    Similarity Matrix: blosum Multiple Alignment Parameters:
    Open Gap Penalty = 10.0   Extend Gap Penalty = 0.1
    Delay Divergent = 40%     Gap Distance = 8
    Similarity Matrix: blosum Processing time: 14.5 seconds

```
con3707.pep    1 MDQYCILGRIGEGAHGIVFKAKHVEPRVGWQCLPSILQTGEIVALKKVAL  50
con3705.pep    1 MDQYCILGRIGEGAHGIVFKAKHVEPRVGWQCLPSILQTGEIVALKKVAL  50
con3703.pep    1 MDQYCILGRIGEGAHGIVFKAKHVET------------GEIVALKKVAL  37
con3702.pep    1 MDQYCILGRIGEGAHGIVFKAKHVET------------GEIVALKKVAL  37
                 ***********************            ******** con3707.pep   51 RRLEDGFPNQALREIKALQEMEDNQYVVQLKAVFPHGGGFVLAFEFMLSD 100
con3705.pep   51 RRLEDGFPNQALREIKALQEMEDNQYVVQLKAVFPHGGGFVLAFEFMLSD 100
con3703.pep   38 RRLEDGFPNQALREIKALQEMEDNQYVVQLKAVFPHGGGFVLAFEFMLSD  87
con3702.pep   38 RRLEDGFPNQALREIKALQEMEDNQYVVQLKAVFPHGGGFVLAFEFMLSD  87
                 ************************************************* con3707.pep  101 LAEVVRHAQRPLAQAQVKSYLQMLLKGVAFCHANNIVHRDLKPANLLISA 150
con3705.pep  101 LAEVVRHAQRPLAQAQVKSYLQMLLKGVAFCHANNIVHRDLKPANLLISA 150
con3703.pep   88 LAEVVRHAQRPLAQAQVKSYLQMLLKGVAFCHANNIVHRDLKPANLLISA 137
con3702.pep   88 LAEVVRHAQRPLAQAQVKSYLQMLLKGVAFCHANNIVHRDLKPANLLISA 137
                 ************************************************* con3707.pep  151 SGQLKIADFGLARVFSPDGSRLYTHQVATRWYRAPELLYGARQYDQGVDL 200
con3705.pep  151 SGQLKIADFGLARVFSPDGSRLYTHQVATRWYRAPELLYGARQYDQGVDL 200
con3703.pep  138 SGQLKIADFGLARVFSPDGSRLYTHQVATR-------------------- 167
con3702.pep  138 SGQLKIADFGLARVFSPDGSRLYTHQVATRWYRAPELLYGARQYDQGVDL 187
                 ****************************** con3707.pep  201 WSVGCIMGELLNGSPLFPGKNDIEQLCYVLRILGTPNPQVWPELTELPDY 250
con3705.pep  201 WSVGCIMGELLNGSPLFPGKNDIEQLCYVLRILGTPNPQVWP-------- 242
con3703.pep  168 -SVGCIMGELLNGSPLFPGKNDIEQLCYVLRILGTPNPQVWPELTELPDY 216
con3702.pep  188 WSVGCIMGELLNGSPLFPGKNDIEQLCYVLRILGTPNPQVWPELTELPDY 237
                  **************************************** con3707.pep  251 NKISFKEQVPMPLEEVLPDVSPQALDLLGQFLLYPPHQRIAASKALLHQY 300
con3705.pep  243 ------EQVPMPLEEVLPDVSPQALDLLGQFLLYPPHQRIAASKALLHQY 286
con3703.pep  217 NKISLKEQVPMPLEEVLPDVSPQALDLLGQFLLYPPHQRIAASKALLHQY 266
con3702.pep  238 NKISFKEQVPMPLEEVLPDVSPQALDLLGQFLLYPPHQRIAASKALLHQY 287
                       ******************************************** con3707.pep  301 FFTAPLPAHPSELPVPQRLGGPAPKAHPGPPHIHDFHVDRPLEESLLNPE 350
con3705.pep  287 FFTAPLPAHPSELPIPQRLGGPAPKAHPGPPHIHDFHVDRPLEESLLNPE 336
con3703.pep  267 FFTAPLPAHPSELPIPQRLGGPAPKAHPGPPHIHDFHVDRPLEESLLNPE 316
con3702.pep  288 FFTAPLPAHPSELPIPQRLGGPAPKAHPGPPHIHDFHVDRPLEESLLNPE 337
                 ************  ******************************* con3707.pep  351 LIRPFILEG 359
con3705.pep  337 LIRPFILEG 345
con3703.pep  317 LIRPFILER 325
con3702.pep  338 LIRPFILER 346
                 ********
```

Clustal W(1.4) multiple sequence alignment

4 Sequences Aligned.            Alignment Score = 42511
Gaps Inserted = 4               Conserved Identities = 932

Pairwise Alignment Mode: Slow                                    FIGURE 2
Pairwise Alignment Parameters:
    Open Gap Penalty = 10.0     Extend Gap Penalty = 5.0

Multiple Alignment Parameters:
    Open Gap Penalty = 10.0     Extend Gap Penalty = 5.0
    Delay Divergent = 40%       Transitions: Weighted Processing time: 107.3 seconds

```
con3702.seq      1           ATGGACCAGTACTGCATCCTGGGCCGCATCGGGGAGGG    38
con3703.seq      1 GGACCTTCTAGAATGGACCAGTACTGCATCCTGGGCCGCATCGGGGAGGG    50
con3707.seq      1           ATGGACCAGTACTGCATCCTGGGCCGCATCGGGGAGGG    38
con3705.seq      1           ATGGACCAGTACTGCATCCTGGGCCGCATCGGGGAGGG    38
                             ************************************** con3702.seq     39 CGCCCACGGCATCGTCTTCAAGGCCAAGCACGTGGAG--------------    75
con3703.seq     51 CGCCCACGGCATCGTCTTCAAGGCCAAGCACGTGGAG--------------    87
con3707.seq     39 CGCCCACGGCATCGTCTTCAAGGCCAAGCACGTGGAGCCGAGGGTGGGCT    88
con3705.seq     39 CGCCCACGGCATCGTCTTCAAGGCCAAGCACGTGGAGCCGAGGGTGGGCT    88
                   ************************************* con3702.seq     76 -------------------------ACTGGCGAGATAGTTGCCCTCAAG    99
con3703.seq     88 -------------------------ACTGGCGAGATAGTTGCCCTCAAG   111
con3707.seq     89 GGCAGTGTCTGCCTTCTATCCTGCAGACTGGCGAGATAGTTGCCCTCAAG   138
con3705.seq     89 GGCAGTGTCTGCCTTCTATCCTGCAGACTGGCGAGATAGTTGCCCTCAAG   138
                                            ************************* con3702.seq    100 AAGGTGGCCCTAAGGCGGTTGGAAGACGGCTTCCCTAACCAGGCCCTGCG   149
con3703.seq    112 AAGGTGGCCCTAAGGCGGTTGGAAGACGGCTTCCCTAACCAGGCCCTGCG   161
con3707.seq    139 AAGGTGGCCCTAAGGCGGTTGGAAGACGGCTTCCCTAACCAGGCCCTGCG   188
con3705.seq    139 AAGGTGGCCCTAAGGCGGTTGGAGGACGGCTTCCCTAACCAGGCCCTGCG   188
                   *********************  *********************** con3702.seq    150 GGAGATTAAGGCTCTGCAGGAGATGGAGGACAATCAGTATGTGGTACAAC   199
con3703.seq    162 GGAGATTAAGGCTCTGCAGGAGATGGAGGACAATCAGTATGTGGTACAAC   211
con3707.seq    189 GGAGATTAAGGCTCTGCAGGAGATGGAGGACAATCAGTATGTGGTACAAC   238
con3705.seq    189 GGAGATTAAGGCTCTGCAGGAGATGGAGGACAATCAGTATGTGGTACAAC   238
                   ************************************************** con3702.seq    200 TGAAGGCTGTGTTCCCACACGGTGGAGGCTTTGTGCTGGCCTTTGAGTTC   249
con3703.seq    212 TGAAGGCTGTGTTCCCACACGGTGGAGGCTTTGTGCTGGCCTTTGAGTTC   261
con3707.seq    239 TGAAGGCTGTGTTCCCACACGGTGGAGGCTTTGTGCTGGCCTTTGAGTTC   288
con3705.seq    239 TGAAGGCTGTGTTCCCACACGGTGGAGGCTTTGTGCTGGCCTTTGAGTTC   288
                   ************************************************** con3702.seq    250 ATGCTGTCGGATCTGGCCGAGGTGGTGCGCCATGCCCAGAGGCCGCTAGC   299
con3703.seq    262 ATGCTGTCGGATCTGGCCGAGGTGGTGCGCCATGCCCAGAGGCCACTAGC   311
con3707.seq    289 ATGCTGTCGGATCTGGCCGAGGTGGTGCGCCATGCCCAGAGGCCACTAGC   338
con3705.seq    289 ATGCTGTCGGATCTGGCCGAGGTGGTGCGCCATGCCCAGAGGCCACTAGC   338
                   ******************************************  ** con3702.seq    300 CCAGGCACAGGTCAAGAGCTACCTGCAGATGCTGCTCAAGGGTGTCGCCT   349
con3703.seq    312 CCAGGCACAGGTCAAGAGCTACCTGCAGATGCTGCTCAAGGGTGTCGCCT   361
con3707.seq    339 CCAGGCACAGGTCAAGAGCTACCTGCAGATGCTGCTCAAGGGTGTCGCCT   388
con3705.seq    339 CCAGGCACAGGTCAAGAGCTACCTGCAGATGCTGCTCAAGGGTGTCGCCT   388
```

(FIGURE 2, cont)

```
                  ****************************************
con3702.seq  350  TCTGCCATGCCAACAACATTGTACATCGGGACCTGAAACCTGCCAACCTG  399
con3703.seq  362  TCTGCCATGCCAACAACATTGTACATCGGGACCTGAAACCTGCCAACCTG  411
con3707.seq  389  TCTGCCATGCCAACAACATTGTACATCGGGACCTGAAACCTGCCAACCTG  438
con3705.seq  389  TCTGCCATGCCAACAACATTGTACATCGGGACCTGAAACCTGCCAACCTG  438
                  ************************************************** con3702.seq  400  CTCATCAGCGCCTCAGGCCAGCTCAAGATAGCGGACTTTGGCCTGGCTCG  449
con3703.seq  412  CTCATCAGCGCCTCAGGCCAGCTCAAGATAGCGGACTTTGGCCTGGCTCG  461
con3707.seq  439  CTCATCAGCGCCTCAGGCCAGCTCAAGATAGCGGACTTTGGCCTGGCTCG  488
con3705.seq  439  CTCATCAGCGCCTCAGGCCAGCTCAAGATAGCGGACTTTGGCCTGGCTCG  488
                  ************************************************** con3702.seq  450  AGTCTTTTCCCCAGACGGCAGCCGCCTCTACACACACCAGGTGGCCACCA  499
con3703.seq  462  AGTCTTTTCCCCAGACGGCAGCCGCCTCTACACACACCAGGTGGCCACCA  511
con3707.seq  489  AGTCTTTTCCCCAGACGGCAGCCGCCTCTACACACACCAGGTGGCCACCA  538
con3705.seq  489  AGTCTTTTCCCCAGACGGCAGCCGCCTCTACACACACCAGGTGGCCACCA  538
                  ************************************************** con3702.seq  500  GGTGGTACCGAGCCCCCGAGCTCCTGTATGGTGCCCGCCAGTATGACCAG  549
con3703.seq  512  GGT-----------------------------------------------  514
con3707.seq  539  GGTGGTACCGAGCCCCCGAGCTCCTGTATGGCGCCCGCCAGTATGACCAG  588
con3705.seq  539  GGTGGTACCGAGCCCCCGAGCTCCTGTATGGTGCCCGCCAGTATGACCAG  588
                  *** con3702.seq  550  GGCGTCGATCTGTGGTCTGTGGGCTGCATCATGGGGGAGCTGTTGAATGG  599
con3703.seq  515  ----------------CTGTGGGCTGCATCATGGGGGAGCTGTTGAATGG  548
con3707.seq  589  GGCGTCGATCTGTGGTCTGTGGGCTGCATCATGGGGGAGCTGTTGAATGG  638
con3705.seq  589  GGCGTCGATCTGTGGTCTGTGGGCTGCATCATGGGGGAGCTGTTGAATGG  638
                                  ********************************** con3702.seq  600  GTCCCCCCTTTTCCCGGGCAAGAACGATATTGAACAGCTTTGCTATGTGC  649
con3703.seq  549  GTCCCCCCTTTTCCCGGGCAAGAACGATATTGAACAGCTTTGCTATGTGC  598
con3707.seq  639  GTCCCCCCTTTTCCCGGGCAAGAACGATATTGAACAGCTTTGCTATGTGC  688
con3705.seq  639  GTCCCCCCTTTTCCCGGGCAAGAACGATATTGAACAGCTTTGCTATGTGC  688
                  ************************************************** con3702.seq  650  TTCGCATCTTGGGCACCCCAAACCCTCAAGTCTGGCCGGAGCTCACTGAG  699
con3703.seq  599  TTCGCATCTTGGGCACCCCAAACCCTCAAGTCTGGCCGGAGCTCACTGAG  648
con3707.seq  689  TTCGCATCTTGGGCACCCCAAACCCTCAAGTCTGGCCGGAGCTCACTGAG  738
con3705.seq  689  TTCGCATCTTGGGCACCCCAAACCCTCAAGTCTGGCCGGAGC--------  730
                  ***************************************** con3702.seq  700  CTGCCGGACTACAACAAGATCTCCTTTAAGGAGCAGGTGCCCATGCCCCT  749
con3703.seq  649  CTGCCGGACTACAACAAGATCTCCCTTAAGGAGCAGGTGCCCATGCCCCT  698
con3707.seq  739  CTGCCGGACTACAACAAGATCTCCTTTAAGGAGCAGGTGCCCATGCCCCT  788
con3705.seq  731  ------------------------------AGGTGCCCATGCCCCT  746
                                                ************** con3702.seq  750  GGAGGAGGTGCTGCCTGACGTCTCTCCCCAGGCATTGGATCTGCTGGGTC  799
con3703.seq  699  GGAGGAGGTGCTGCCTGACGTCTCTCCCCAGGCATTGGATCTGCTGGGTC  748
con3707.seq  789  GGAGGAGGTGCTGCCTGACGTCTCTCCCCAGGCATTGGATCTGCTGGGTC  838
con3705.seq  747  GGAGGAGGTGCTGCCTGACGTCTCTCCCCAGGCATTGGATCTGCTGGGTC  796
                  ************************************************** con3702.seq  800  AATTCCTTCTCTACCCTCCTCACCAGCGCATCGCAGCTTCCAAGGCTCTC  849
con3703.seq  749  AATTCCTTCTCTACCCTCCTCACCAGCGCATCGCAGCTTCCAAGGCTCTC  798
con3707.seq  839  AATTCCTTCTCTACCCTCCTCACCAGCGCATCGCAGCTTCCAAGGCTCTC  888
con3705.seq  797  AATTCCTTCTCTACCCTCCTCACCAGCGCATCGCAGCTTCCAAGGCTCTC  846
                  **************************************************
```

(FIGURE 2 cont)

```
con3702.seq   850 CTCCATCAGTACTTCTTCACAGCTCCCCTGCCTGCCCATCCATCTGAGCT  899
con3703.seq   799 CTCCATCAGTACTTCTTCACAGCTCCCCTGCCTGCCCATCCATCTGAGCT  848
con3707.seq   889 CTCCATCAGTACTTCTTCACAGCTCCCCTGCCTGCCCATCCATCTGAGCT  938
con3705.seq   847 CTCCATCAGTACTTCTTCACAGCTCCCCTGCCTGCCCATCCATCTGAGCT  896
                  ************************************************** con3702.seq   900 GCCGATTCCTCAGCGTCTAGGGGGACCTGCCCCCAAGGCCCATCCAGGGC  949
con3703.seq   849 GCCGATTCCTCAGCGTCTAGGGGGACCTGCCCCCAAGGCCCATCCAGGGC  898
con3707.seq   939 GCCGGTTCCTCAGCGTCTAGGGGGACCTGCCCCCAAGGCCCATCCAGGGC  988
con3705.seq   897 GCCGATTCCTCAGCGTCTAGGGGGACCTGCCCCCAAGGCCCATCCAGGGC  946
                  **  ****************************************** con3702.seq   950 CCCCCCACATCCATGACTTCCACGTGGACCGGCCTCTTGAGGAGTCGCTG  999
con3703.seq   899 CCCCCCACATCCATGACTTCCACGTGGACCGGCCTCTTGAGGAGTCGCTG  948
con3707.seq   989 CCCCCCACATCCATGACTTCCACGTGGACCGGCCTCTTGAGGAGTCGCTG 1038
con3705.seq   947 CCCCCCACATCCATGACTTCCACGTGGACCGGCCTCTTGAGGAGTCGCTG  996
                  ************************************************** con3702.seq  1000 TTGAACCCAGAGCTGATTCGGCCCTTCATCCTGGAGGGGTGAGGATCCTG 1049
con3703.seq   949 TTGAACCCAGAGCTGATTCGGCCCTTCATCCTGGAGAGGTGAGGATCCTG  998
con3707.seq  1039 TTGAACCCAGAGCTGATTCGGCCCTTCATCCTGGAGGGGTGAGGATCCTG 1088
con3705.seq   997 TTGAACCCAGAGCTGATTCGGCCCTTCATCCTGGAGGGGTGA         1038
                  ****************************************  ** con3702.seq  1050 AGAA 1053
con3703.seq   999 AGAA 1002
con3707.seq  1089 AGAA 1092
con3705.seq  1039      1038
```

HUMAN CYCLIN-DEPENDENT KINASE (HPNQALRE)

CROSS-REFERENCE TO RELATED APPLICATIONS

This application is a divisional (and claims the benefit of priority under 35 USC 120) of U.S. application Ser. No. 10/663,896, filed Sep. 16, 2003, now U.S. Pat. No. 7,250,256, which is a continuation of U.S. application Ser. No. 09/464,065 filed Dec. 15, 1999 (abandoned) which claims priority benefit of provisional Application Ser. No. 60/112,497 (expired) filed Dec. 16, 1998. The disclosures of the prior applications are considered part of (and are incorporated by reference in) the disclosure of this application.

TECHNICAL FIELD

The invention relates to the area of protein kinases. More particularly, the invention relates to cyclin-dependent protein kinases.

BACKGROUND OF THE INVENTION

The pathways responsible for regulating mitosis and migration and for transducing environmental stress signals in cells have not been fully described. Such proteins can be manipulated, for example, to protect cells against stress due to disease or environmental conditions and to treat disorders involving alterations in mitosis or migration, such as neoplasia. Thus, there is a need in the art for the identification of proteins which are involved in these pathways.

SUMMARY OF THE INVENTION

The present invention provides, in various embodiments, reagents and methods for diagnosing and treating neoplasia, as well as regulating the cell cycle.

One embodiment of the invention provides isolated polypeptides having at least 223 contiguous amino acids of an hPNQALRE protein selected from the group consisting of SEQ ID NO:4, SEQ ID NO:6 and SEQ ID NO:8. Other related embodiments provide isolated polypeptides comprising amino acid sequences that are at least 65%, 70%, 75%, 80%, 85%, 90%, 91%, 92%, 93%, 94%, 95%, 96%, 97%, 98%, 99% or 100% identical to amino acids 26-38 and/or amino acids 181-201 of SEQ ID NO:6. Also provided are isolated polypeptides comprising an amino acid sequence selected from the group consisting of SEQ ID NO:2, SEQ ID NO:4, SEQ ID NO:6 and SEQ ID NO:8.

Other embodiments of the present invention provide fusion proteins comprising first and second protein segments which are fused together by means of a peptide bond. First proteins of the present invention include, for example, at least 223 contiguous amino acids of an amino acid sequence selected from the group consisting of SEQ ID NO:4, SEQ ID NO:6 and SEQ ID NO:8. Also provided are fusion proteins in which the first protein segment comprises an amino acid sequence that is at least 65%, 70%, 75%, 80%, 85%, 90%, 91%, 92%, 93%, 94%, 95%, 96%, 97%, 98%, 99% or 100% identical to amino acids 26-38 or amino acids 181-201 of SEQ ID NO:6.

Still other embodiments of the present invention include preparations of antibodies that specifically bind to a protein comprising an amino acid sequence of SEQ ID NO:4, SEQ ID NO:6 and/or SEQ ID NO:8. Related embodiments include antibody preparations that specifically bind to an epitope defined in whole or in part by amino acids 26-38 of SEQ ID NO:6 and/or SEQ ID NO:8 and/or amino acids 181-201 of SEQ ID NO:6.

Further embodiments provide cDNA molecules that encode polypeptides comprising at least 223 contiguous amino acids of an hPNQALRE protein selected from the group consisting of SEQ ID NO:4, SEQ ID NO:6 and SEQ ID NO:8. Similar embodiments include cDNA molecules that encode polypeptides comprising an amino acid sequence that is at least 65%, 70%, 75%, 80%, 85%, 90%, 91%, 92%, 93%, 94%, 95%, 96%, 97%, 98%, 99% or 100% identical to amino acids 26-38 and/or 181-201 of SEQ ID NO:6. The present invention also provides cDNAs that encode polypeptides comprising an amino acid sequence selected from the group consisting of SEQ ID NO:2, SEQ ID NO:4, SEQ ID NO:6 and SEQ ID NO:8. Inventive cDNA molecules are also provided that comprise a nucleic acid sequence that is at least 65%, 70%, 75%, 80%, 85%, 90%, 91%, 92%, 93%, 94%, 95%, 96%, 97%, 98%, 99% or 100% identical to nucleotides 76-114 of SEQ ID NO:5 and/or that is at least 65%, 70%, 75%, 80%, 85%, 90%, 91%, 92%, 93%, 94%, 95%, 96%, 97%, 98%, 99% or 100% identical to nucleotides 503-564 of SEQ ID NO:3 and/or that is at least 65%, 70%, 75%, 80%, 85%, 90%, 91%, 92%, 93%, 94%, 95%, 96%, 97%, 98%, 99% or 100% identical to nucleotides 542-603 of SEQ ID NO:5. Also provided are cDNA molecules that comprise a nucleotide sequence selected from the group consisting of SEQ ID NO:1, SEQ ID NO:3, SEQ ID NO:5 and SEQ ID NO:7.

Still further embodiments of the present invention include isolated subgenomic polynucleotides or the complements thereof that comprise a nucleotide sequence that hybridizes under stringent conditions to nucleotides 76-114 of SEQ ID NO:5 and/or nucleotides 503-564 of SEQ ID NO:3.

Other inventive embodiments include constructs comprising a promoter and a polynucleotide segment encoding at least 223 amino acids of an amino acid sequence selected from the group consisting of SEQ ID NO:4, SEQ ID NO:6 and SEQ ID NO:8. By exemplary constructs, the polynucleotide segment is located downstream from the promoter and transcription of the polynucleotide segment initiates at the promoter. Similar embodiments include constructs comprising a promoter and a polynucleotide segment encoding a polypeptide comprising an amino acid sequence that is at least 65%, 70%, 75%, 80%, 85%, 90%, 91%, 92%, 93%, 94%, 95%, 96%, 97%, 98%, 99% or 100% identical to amino acids 26-38 and/or amino acids 181-201 of SEQ ID NO:6. The polynucleotide segment may be located downstream from the promoter and transcription of the polynucleotide segment may initiate at the promoter. Inventive constructs also comprise a promoter and a polynucleotide segment encoding a polypeptide comprising an amino acid sequence selected from the group consisting of SEQ ID NO:2, SEQ ID NO:4, SEQ ID NO:6 and SEQ ID NO:8.

Other inventive embodiments include host cells that comprise any of the constructs provided herein.

Further embodiments provide homologously recombinant cells that incorporate a new transcription initiation unit. New transcription initiation units of the present invention may comprise an exogenous regulatory sequence, an exogenous exon and a splice donor site. The new transcription initiation unit may be located upstream of the coding sequence of a gene having a coding sequence selected from the group consisting of SEQ ID NO:1, SEQ ID NO:3, SEQ ID NO:5 and SEQ ID NO:7. The exogenous regulatory sequence may direct transcription of the coding sequence of the gene.

Still further embodiments provide methods of diagnosing or prognosing neoplasia. Such methods may comprise the step of comparing expression of a first hPNQALRE gene in a first tissue suspected of being neoplastic with the expression of a second hPNQALRE gene of a second tissue that is normal. The first and second hPNQALRE genes may comprise coding sequences selected from the group consisting of SEQ ID NO:1, SEQ ID NO:3, SEQ ID NO:5 and SEQ ID NO:7. By these methods, over-expression of the first hPNQALRE gene in the first tissue indicates neoplasia in the first tissue. By similar methods of diagnosing or prognosing neoplasia, the first and/or second hPNQALRE genes may comprise a coding sequence selected from the group consisting of nucleotides 76-114 of SEQ ID NO:5, nucleotides 503-564 of SEQ ID NO:3 and/or nucleotides 542-603 of SEQ ID NO:5.

The present invention thus provides the art with amino acid sequences of hPNQALRE, a unique member of the cyclin-dependent kinase family, and DNA sequences which encode hPNQALRE. The invention can be used, inter alia, to treat neoplasia and other proliferative diseases.

BRIEF DESCRIPTION OF THE DRAWINGS

FIG. 1 compares the amino acid sequences of the four forms of hPNQALRE having the amino acid sequences of con3703.pep (SEQ ID NO: 2), con3702.pep (SEQ ID NO: 4), con3707.pep (SEQ ID NO: 6), and con3705.pep (SEQ ID NO: 8).

FIG. 2 compares nucleotide coding sequences which encode the four forms of hPNQALRE having the nucleotide sequences of con3703.seq (SEQ ID NO: 1), con3702.seq (SEQ ID NO: 3), con3707.seq (SEQ ID NO: 5), and con3705.seq (SEQ ID NO: 7).

DETAILED DESCRIPTION OF THE INVENTION

A novel human cyclin-dependent kinase termed hPNQALRE is a discovery of the present invention. hPNQALRE is a member of the cyclin-dependent kinase family. hPNQALRE is over-expressed in tumors and can be used both diagnostically and therapeutically.

Amino acid sequences of four forms of human hPNQALRE protein (SEQ ID NOS:2, 4, 6, and 8), as well as polynucleotide sequences which encode the four forms of hPNQALRE (SEQ ID NOS:1, 3, 5, and 7) are disclosed herein. All key positions of cyclin-dependent kinases are conserved in this protein. The regulatory phosphorylation sites at the N-terminus of the molecule found in cdk2 (threonine at position 14 and tyrosine at position 15) are replaced in hPNQALRE by alanine and histidine, respectively, similar to the CDK7-type cyclin-dependent kinases, which also have two residues which cannot be phosphorylated (glutamine and phenylalanine) at these positions. Regulatory phosphorylation sites of cyclin-dependent kinases are described inter alia in Shuttleworth, *Progr. Cell Cycle Res.* 1, 229-40 (1995); Lew & Kombluth, *Curr. Opin. Cell Biol.* 8, 795-804 (1996); and Morgan, *Ann. Rev. Cell. Biol.* 13, 261-91 (1997). The sequence motif which characterizes the cyclin binding domain of the cyclin-dependent kinases (PSTAIRE in cdk2; SEQ ID NO:15) is replaced in hPNQALRE by the sequence PNQALRE (SEQ ID NO:9), indicating that hPNQALRE has a distinct specificity for its regulatory cyclin subunit.

Various amino acids of hPNQALRE can be substituted to form hPNQALRE variants with one or more altered biological activities. For example the cyclin-dependent kinase activity or cyclin binding domain of hPNQALRE can be altered, or substitutions can be made which permit the protein to be phosphorylated. Such substitutions can provide hPNQALRE with altered regulation or a particular subset of biological activities as compared to wild type hPNQALRE. Cyclin binding domains of other cyclin-dependent kinases, such as PFTAIRE (SEQ ID NO:10), PISSLRE (SEQ ID NO:11), PITALRE (SEQ ID NO:12), PLSTIRE (SEQ ID NO:13), PISTVRE (SEQ ID NO:14), PSTAIRE (SEQ ID NO:15), and NRTALRE (SEQ ID NO:16), can be substituted for the cyclin binding domain of hPNQALRE, PNQALRE (SEQ ID NO:9; amino acids 44-51 of SEQ ID NOS:2 or 4; amino acids 58-64 of SEQ ID NOS:6 and 8) in order to change the cyclin binding specificity of hPNQALRE. Cyclin-dependent kinase activity of hPNQALRE can be modified, for example, by substituting an asparagine for the aspartic acid at position 145; this substitution results in a "kinase-dead" form of hPNQALRE.

Various substitutions can also be made in order to permit hPNQALRE to be phosphorylated. For example, substitution of a phenylalanine or a tyrosine for the histidine at position 15, or substitution of a threonine for the alanine at position 14, permit phosphorylation of hPNQALRE. Other substitutions which affect properties of hPNQALRE will occur to those of skill in the art and can be made to hPNQALRE protein using standard recombinant DNA techniques.

Other amino acid substitutions which do not affect the kinase or cyclin binding activities of hPNQALRE can occur naturally or can be made in the laboratory, to form biologically active hPNQALRE variants. Biologically active variants of hPNQALRE are involved in cell-cycle regulation, display cyclin-dependent kinase activity, and are over-expressed in tumors. Guidance in determining which amino acid residues may be substituted, inserted, or deleted without abolishing biological or immunological activity may be found using computer programs well known in the art, such as DNASTAR software.

Preferably, amino acid substitutions in biologically active hPNQALRE variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids. It is reasonable to expect that an isolated replacement of a leucine with an isoleucine or valine, an aspartate with a glutamate, a threonine with a serine, or a similar replacement of an amino acid with a structurally related amino acid will not have a major effect on the binding properties of the resulting molecule, especially if the replacement does not involve an amino acid at the cyclin-binding site of hPNQALRE or its kinase domain.

Biologically active hPNQALRE variants include glycosylated forms, aggregative conjugates with other molecules, and covalent conjugates with unrelated chemical moieties. Covalent variants can be prepared by linking functionalities to groups which are found in the amino acid chain or at the N- or C-terminal residue, as is known in the art. Biologically active hPNQALRE variants also include allelic variants, species variants, and muteins. Truncations or deletions of regions which do not affect the cyclin-dependent kinase activity of hPNQALRE are also hPNQALRE variants.

Whether an amino acid substitution results in a functional hPNQALRE protein or polypeptide can readily be determined, for example, by assaying its cyclin-dependent kinase activity. Assays for cyclin-dependent kinase activity are taught, for example, in Lock et al., 1997, *Cancer Chemother. Pharmacol.* 39:399-409. Preferred naturally or non-naturally occurring biologically active hPNQALRE variants have amino acid sequences which are at least 65%, 70%, 75%, 80%, 85%, 90%, 91%, 92%, 93%, 94%, 95%, 96%, 97%, 98%, 99% or 100% identical to amino acid sequences shown in SEQ ID NOS:2, 4, 6, or 8. More preferably, the molecules are at least 98% or 99% identical. Percent identity can be calculated using any method or algorithm known in the art. A non-limiting example is the Smith-Waterman homology search algorithm, using an affine gap search with the following parameters: a gap open penalty of 12 and a gap extension penalty of 1. The Smith-Waterman homology search algorithm is taught in Smith and Waterman, *Adv. Appl. Math.* (1981) 2:482-489.

hPNQALRE polypeptides contain less than full-length hPNQALRE and comprise at least 223, 225, 250, 275, 300, or 325 or more contiguous amino acids of an hPNQALRE protein. hPNQALRE polypeptides can comprise the cyclin binding domain of hPNQALRE, PNQALRE (SEQ ID NO:9; amino acids 44-51 of SEQ ID NOS:2 or 4 or amino acids 58-64 of SEQ ID NOS:6 and 8), or can be chimeric polypeptides which comprise hPNQALRE amino acid sequences together with cyclin binding domains of other cyclin-dependent kinases, as disclosed above. Polypeptides in which various amino acid substitutions have been made so as to permit hPNQALRE to be phosphorylated or to decrease kinase activity of hPNQALRE can also be constructed.

hPNQALRE polypeptides of the present invention may comprise amino acids 26-38 of SEQ ID NO:6 or SEQ ID NO:8. Additionally, hPNQALRE polypeptides may comprise amino acids 181-201 of SEQ ID NO:6 or SEQ ID NO:8 or amino acids 168-188 of SEQ ID NO:4.

The present invention contemplates variants of hPNQALRE polypeptides which are at least 65%, 70%, 75%, 80%, 85%, 90%, 91%, 92%, 93%, 94%, 95%, 96%, 97%, 98%, 99% or 100% identical to the polypeptides of SEQ ID NO:2, SEQ ID NO:4, SEQ ID NO:6 or SEQ ID NO:8. For example, the present invention provides hPNQALRE polypeptides that are at least 65%, 70%, 75%, 80%, 85%, 90%, 91%, 92%, 93%, 94%, 95%, 96%, 97%, 98%, 99% or 100% identical to amino acids 26-38 of SEQ ID NO:6 or SEQ ID NO:8 or that are at least 65%, 70%, 75%, 80%, 85%, 90%, 91%, 92%, 93%, 94%, 95%, 96%, 97%, 98%, 99% or 100% identical to amino acids 181-201 of SEQ ID NO:6 or SEQ ID NO:8 or amino acids 168-188 of SEQ ID NO:4.

hPNQALRE can be isolated from hPNQALRE-producing human cells, such as spleen, thymus, prostate, testis, small intestine, colon, peripheral blood lymphocytes, heart, brain, placenta, lung, liver, skeletal muscle, kidney, or pancreas, using standard biochemical methods. An isolated and purified hPNQALRE protein or polypeptide is separated from other compounds which normally associate with an hPNQALRE protein or polypeptide in a cell, such as cyclin or other proteins, carbohydrates, lipids, or: subcellular organelles. A preparation of isolated and purified hPNQALRE proteins or polypeptides is at least 80% pure; preferably, the preparations are 90%, 95%, or 99% pure.

hPNQALRE proteins and polypeptides can also be produced by recombinant DNA methods or by synthetic chemical methods. For production of recombinant hPNQALRE proteins or polypeptides, coding sequences selected from the hPNQALRE nucleotide sequences shown in SEQ ID NOS:1, 3, 5, and 7 or variants of those sequence which encode, for example, an hPNQALRE protein or biologically active or altered hPNQALRE variants, can be expressed in prokaryotic or eukaryotic expression systems. Bacterial, yeast, insect, or mammalian expression systems can be used, as is known in the art. Enzymes can be used to generate hPNQALRE polypeptides by enzymatic proteolysis of full-length hPNQALRE protein.

Alternatively, synthetic chemical methods, such as solid phase peptide synthesis, can be used to synthesize an hPNQALRE protein or polypeptide. General means for the production of peptides, analogs or derivatives are outlined in CHEMISTRY AND BIOCHEMISTRY OF AMINO ACIDS, PEPTIDES, AND PROTEINS—A SURVEY OF RECENT DEVELOPMENTS, B. Weinstein, ed. (1983). Moreover, substitution of D-amino acids for the normal L-stereoisomer can be carried out to increase the half-life of the molecule. Biologically active hPNQALRE or altered variants can be similarly produced.

Fusion proteins comprising at least 223, 225, 250, 275, 300, or 315 or more contiguous hPNQALRE amino acids can also be constructed. hPNQALRE fusion proteins are useful for generating antibodies which specifically bind to hPNQALRE epitopes and for use in various assay systems. For example, hPNQALRE fusion proteins can be used to identify proteins which interact with hPNQALRE protein, such as different cyclins, and influence its function. Physical methods, such as protein affinity chromatography, or library-based assays for protein-protein interactions, such as the yeast two-hybrid or phage display systems, can also be used for this purpose. Such methods are well known in the art and can also be used as drug screens.

An hPNQALRE fusion protein comprises two protein segments fused together by means of a peptide bond. The first protein segment can be N-terminal or C-terminal, as is convenient. The first protein segment comprises at least 223, 225, 250, 275, 300, or 315 or more contiguous amino acids of an hPNQALRE protein. The amino acids can be selected from the amino acid sequences shown in SEQ ID NOS:2, 4, 6, and 8 or from a biologically active or altered variant of those sequences. Preferred fusion proteins of the present invention may comprise amino acids 26-38 of SEQ ID NO:6 or SEQ ID NO:8. Also preferred are fusion proteins that comprise amino acids 181-201 of SEQ ID NO:6 or SEQ ID NO:8 or amino acids 168-188 of SEQ ID NO:4. The first protein segment can also comprise a full-length hPNQALRE protein or variant. The first protein segment can be located at the N- or C-terminal of the fusion protein, as is convenient.

The second protein segment can be a full-length protein or a protein fragment or polypeptide. Proteins commonly used in fusion protein construction include β-galactosidase, β-glucoronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Epitope tags can be used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex A DNA binding domain (DBD) fusions, GAL4 DNA binding domain fusions, and herpes simplex virus (HSV) BP16 protein fusions.

hPNQALRE fusion proteins can be made by covalently linking the first and second protein segments or by standard procedures in the art of molecular biology. Recombinant DNA methods can be used to prepare hPNQALRE fusion proteins, for example, by making a DNA construct which comprises coding sequences selected from SEQ ID NOS:1, 3, 5, or 7 in proper reading frame with nucleotides encoding the second protein segment and expressing the DNA construct in a host cell, as is known in the art. Many kits for constructing fusion proteins are available from companies which supply research labs with tools for experiments, including, for example, Promega Corporation (Madison, Wis.), Stratagene (La Jolla, Calif.), Clontech (Mountain View, Calif.), Santa Cruz Biotechnology (Santa Cruz, Calif.), MBL International Corporation (MIC; Watertown, Mass.), and Quantum Biotechnologies (Montreal, Canada).

Isolated and purified hPNQALRE proteins, polypeptides, biologically active or altered variants, or fusion proteins can be used as immunogens, to obtain preparations of antibodies which specifically bind to epitopes of an hPNQALRE protein having an amino acid sequence shown in SEQ ID NOS:2, 4, 6, or 8 or a biologically active or altered hPNQALRE variant. Preferably, the antibodies can distinguish between hPNQALRE and other cyclin-dependent kinases, for example by binding to the cyclin-binding site of hPNQALRE. More preferably, antibodies of the present invention will bind to an epitope defined in whole or in part by amino acids 26-38 of SEQ ID NO:6 or SEQ ID NO:8. Also preferred are antibodies that bind to an epitope defined in whole or in part by amino acids 181-201 of SEQ ID NO:6 or SEQ ID NO:8 or amino acids 168-188 of SEQ ID NO:4. Typically, at least 6, 8, 10, or 12 contiguous amino acids are required to form an hPNQALRE epitope. However, epitopes which involve non-contiguous amino acids may require more, e.g., at least 15, 25, or 50 amino acids.

Antibodies which specifically bind to epitopes of hPNQALRE proteins, polypeptides, fusion proteins, or biologically active variants can be used in immunochemical assays, including but not limited to Western blots, ELISAs, radioimmunoassays, immunohistochemical assays, immunoprecipitations, or other immunochemical assays known in the art. Typically, antibodies of the invention provide a detection signal at least 5-, 10-, or 20-fold higher than a detection signal provided with other proteins when used in such immunochemical assays. Preferably, antibodies which specifically bind to hPNQALRE epitopes do not detect other proteins in immunochemical assays and can immunoprecipitate hPNQALRE protein or polypeptides from solution.

Epitopes of hPNQALRE which are particularly antigenic can be selected, for example, by routine screening of hPNQALRE polypeptides for antigenicity or by applying a theoretical method for selecting antigenic regions of a protein to the amino acid sequences shown in SEQ ID NOS:2, 4, 6, or 8. Such methods are taught, for example, in Hopp and Wood, *Proc. Natl. Acad. Sci. U.S.A.* 78, 3824-28 (1981), Hopp and Wood, *Mol. Immunol.* 20, 483-89 (1983), and Sutcliffe et al., *Science* 219, 660-66 (1983).

Any type of antibody known in the art can be generated to bind specifically to hPNQALRE epitopes. For example, preparations of polyclonal and monoclonal antibodies can be made using standard methods which are well known in the art. Similarly, single-chain antibodies can also be prepared. Single-chain antibodies which specifically bind to hPNQALRE epitopes can be isolated, for example, from single-chain immunoglobulin display libraries, as is known in the art. The library is "panned" against hPNQALRE amino acid sequences, and a number of single chain antibodies which bind with high-affinity to different epitopes of hPNQALRE protein can be isolated. Hayashi et al., 1995, *Gene* 160:129-30. Single-chain antibodies can also be constructed using a DNA amplification method, such as the polymerase chain reaction (PCR), using hybridoma cDNA as a template. Thirion et al., 1996, *Eur. J. Cancer Prev.* 5:507-11.

Single-chain antibodies can be mono- or bispecific, and can be bivalent or tetravalent. Construction of tetravalent, bispecific single-chain antibodies is taught, for example, in Coloma and Morrison, 1997, *Nat. Biotechnol.* 15:159-63. Construction of bivalent, bispecific single-chain antibodies is taught inter alia in Mallender and Voss, 1994, *J. Biol. Chem.* 269:199-206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology. Verhaar et al., 1995, *Int. J. Cancer* 61:497-501; Nicholls et al., 1993, *J. Immunol. Meth.* 165:81-91.

Monoclonal and other antibodies can also be "humanized" in order to prevent a patient from mounting an immune response against the antibody when it is used therapeutically. Such antibodies may be sufficiently similar in sequence to human antibodies to be used directly in therapy or may require alteration of a few key residues. Sequence differences between, for example, rodent antibodies and human sequences can be minimized by replacing residues which differ from those in the human sequences, for example, by site directed mutagenesis of individual residues, or by grafting of entire complementarity determining regions. Alternatively, one can produce humanized antibodies using recombinant methods, as described in GB2188638B. Antibodies which specifically bind to hPNQALRE epitopes can contain antigen binding sites which are either partially or fully humanized, as disclosed in U.S. Pat. No. 5,565,332.

Other types of antibodies can be constructed and used in methods of the invention. For example, chimeric antibodies can be constructed as disclosed, for example, in WO 93/03151. Binding proteins which are derived from immunoglobulins and which are multivalent and multispecific, such as the "diabodies" described in WO 94/13804, can also be prepared.

Antibodies of the invention can be purified by methods well known in the art. For example, antibodies can be affinity purified by passing the antibodies over a column to which an hPNQALRE protein, polypeptide, biologically active variant, or fusion protein is bound. The bound antibodies can then be eluted from the column, using a buffer with a high salt concentration.

hPNQALRE-specific binding polypeptides other than antibodies can also be generated. hPNQALRE-specific binding polypeptides are polypeptides which bind with hPNQALRE or its variants and which have a measurably higher binding affinity for hPNQALRE and polypeptide derivatives of hPNQALRE than for other polypeptides tested for binding. Higher affinity by a factor of 10 is preferred, more preferably a factor of 100. Such polypeptides can be found, for example, using the yeast two-hybrid system.

Antibodies can be used, inter alia, to detect wild-type hPNQALRE protein in human tissue and fractions thereof. The antibodies can also be used to detect the presence of mutations in the hPNQALRE gene which result in under- or overexpression of an hPNQALRE protein or in expression of an hPNQALRE protein with altered size or electrophoretic mobility. Optionally, antibodies of the invention can be used to block hPNQALRE cyclin binding sites or to alter effective levels of functional hPNQALRE protein. Alternatively, Antibodies may be used to detect polypeptides comprising amino acids 26-38 of SEQ ID NO:6 or SEQ ID NO:8. Preferred antibodies will bind to and block the biological activity defined by the T-loop region which includes amino acids 181-201 of SEQ ID NO:6 or SEQ ID NO:8 or amino acids 168-188 of SEQ ID NO:4.

The invention also provides subgenomic polynucleotides which encodes hPNQALRE proteins, polypeptides, biologically active or altered variants, fusion proteins, and the like. hPNQALRE subgenomic polynucleotides contain less than a whole chromosome and can be double- or single-stranded. Preferably, the polynucleotides are intron-free.

hPNQALRE subgenomic polynucleotides can comprise at least 1562, 1563, 1670, 1575, 1800, 1859, 1900, 1950, 2000, 2050, or 2100 or more contiguous nucleotides selected from the nucleotide sequences shown in SEQ ID NOS:1, 3, 5, or 7 or their complements. Complementary nucleotide sequences can be used provide hPNQALRE antisense oligonucleotides. Preferred antisense oligonucleotides that are encompassed by nucleotides 76-114 of SEQ ID NO:5 or SEQ ID NO:7. Also preferred are antisense oligonucleotides that are encompassed by nucleotides 503-564 of SEQ ID NO:3, nucleotides 542-603 of SEQ ID NO:5 or SEQ ID NO:7. hPNQALRE subgenomic polynucleotides also include polynucleotides which encode hPNQALRE-specific single-chain antibodies, ribozymes, and biologically active or altered hPNQALRE variants.

Degenerate nucleotide sequences encoding amino acid sequences of hPNQALRE protein or biologically active hPNQALRE variants, as well as homologous nucleotide sequences which are at least 65%, 70%, 75%, 80%, 85%, 90%, 91%, 92%, 93%, 94%, 95%, 96%, 97%, 98%, 99% or 100% identical to the nucleotide sequences shown in SEQ ID NOS:1, 3, 5, or 7 are also hPNQALRE subgenomic polynucleotides. Preferred subgenomic polynucleotides include nucleotides which are at least 65%, 70%, 75%, 80%, 85%, 90%, 91%, 92%, 93%, 94%, 95%, 96%, 97%, 98%, 99% or 100% identical to 76-114 of SEQ ID NO:5 or SEQ ID NO:7 as well as nucleotides 503-564 of SEQ ID NO:3 and nucleotides 542-603 of SEQ ID NO:5 or SEQ ID NO:7. Percent sequence identity may be determined using computer programs which employ the Smith-Waterman algorithm, for example as implemented in the MPSRCH program (Oxford Molecular), using an affine gap search with the following parameters: a gap open penalty of 12 and a gap extension penalty of 1.

Nucleotide sequences which hybridize to the coding sequences shown in SEQ ID NOS:1, 3, 5, and 7 or their complements with at most 1, 2, 3, 4, 5, 10, 15, 20, 25, 30, or 35% basepair mismatches are also hPNQALRE subgenomic polynucleotides of the invention. Preferred nucleotide sequences will hybridize with at most 1, 2, 3, 4, 5, 10, 15, 20, 25, 30, or 35% basepair mismatches to nucleotides 76-114 of SEQ ID NO:5 or SEQ ID NO:7 as well as nucleotides 503-564 of SEQ ID NO:3 and nucleotides 542-603 of SEQ ID NO:5 or SEQ ID NO:7. For example, using the following wash conditions—2×SSC (0.3 M sodium chloride, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous hPNQALRE sequences can be identified which contain at most about 25-30% basepair mismatches with SEQ ID NOS:1, 3, 5, or 7 or their complements. More preferably, homologous nucleic acid strands contain 15-25% basepair mismatches, even more preferably 5-15% basepair mismatches.

Species homologs of hPNQALRE subgenomic polynucleotides of the invention can also be identified by making suitable probes or primers and screening cDNA expression libraries from other species, such as mice, monkeys, yeast, or bacteria. It is well known that the $T_m$ of a double-stranded DNA decreases by 1-1.5° C. with every 1% decrease in homology (Bonner et al., *J. Mol. Biol.* 81, 123 (1973).

Homologous hPNQALRE polynucleotides can therefore be identified, for example, by hybridizing a putative homologous hPNQALRE polynucleotide with a polynucleotide having the nucleotide sequence of SEQ ID NOS:1, 3, 5, or 7, comparing the melting temperature of the test hybrid with the melting temperature of a hybrid comprising a polynucleotide having SEQ ID NOS:1, 3, 5, or 7 and a polynucleotide which is perfectly complementary to that sequence, and calculating the number or percent of basepair mismatches within the test hybrid.

Nucleotide sequences which hybridize to the coding sequences shown in SEQ ID NOS:1, 3, 5, or 7 or their complements following stringent hybridization and/or wash conditions are also hPNQALRE subgenomic polynucleotides of the invention. Stringent wash conditions are well known and understood in the art and are disclosed, for example, in Sambrook et al., MOLECULAR CLONING: A LABORATORY MANUAL, 2d ed., 1989, at pages 9.50-9.51. Preferred species homologs of hPNQALRE subgenomic polynucleotides will hybridize under stringent conditions to nucleotides 76-114 of SEQ ID NO:5 or SEQ ID NO:7 or to nucleotides 503-564 of SEQ ID NO:3 and nucleotides 542-603 of SEQ ID NO:5 or SEQ ID NO:7.

Typically, for stringent hybridization conditions, a combination of temperature and salt concentration should be chosen that is approximately 12-20° C. below the calculated $T_m$ of the hybrid under study. The $T_m$ of a hybrid between the hPNQALRE sequence shown in SEQ ID NOS:1, 3, 5, or 7 and a polynucleotide sequence which is 65%, 75%, 85%, 90%, 95%, 96%, 97%, 98%, or 99% identical can be calculated, for example, using the equation of Bolton and McCarthy, *Proc. Natl. Acad. Sci. U.S.A.* 48, 1390 (1962):

$$T_m = 81.5° C. - 16.6(\log_{10}[Na^+]) + 0.41(\% G+C) - 0.63(\% \text{ formamide}) - 600/l),$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

hPNQALRE subgenomic polynucleotides can be isolated and purified free from other nucleotide sequences using standard nucleic acid purification techniques. For example, restriction enzymes and probes can be used to isolate polynucleotide fragments which comprise nucleotide sequences encoding an hPNQALRE protein or variant. Isolated and purified subgenomic polynucleotides are in preparations which are free or at least 90% free of other molecules.

Complementary DNA (cDNA) molecules which encode hPNQALRE proteins are also hPNQALRE subgenomic polynucleotides of the invention. hPNQALRE cDNA molecules can be made with standard molecular biology techniques, using hPNQALRE mRNA as a template. hPNQALRE cDNA molecules can thereafter be replicated using molecular biology techniques known in the art and disclosed in manuals such as Sambrook et al., 1989. An amplification technique, such as the polymerase chain reaction (PCR), can be used to obtain additional copies of subgenomic polynucleotides of the invention, using either human genomic DNA or cDNA as a template.

Alternatively, synthetic chemistry techniques can be used to synthesize hPNQALRE subgenomic polynucleotide molecules of the invention. The degeneracy of the genetic code allows alternate nucleotide sequences to be synthesized which will encode an hPNQALRE protein having the amino acid sequences shown in SEQ ID NOS:2, 4, 6, or 8 or a biologically active variant of those sequences. All such nucleotide sequences are within the scope of the present invention.

The invention also provides polynucleotide probes which can be used to detect hPNQALRE sequences, for example, in hybridization protocols such as Northern or Southern blotting or in situ hybridization. Polynucleotide probes of the invention comprise at least 12, 13, 14, 15, 16, 17, 18, 19, 20, 30, or 40 or more contiguous nucleotides selected from SEQ ID NOS:1, 3, 5, or 7. Preferred probes, comprise at least 12, 13, 14, 15, 16, 17, 18, 19, 20, 30, or 40 or more contiguous nucleotides selected from nucleotides 76-114 of SEQ ID NO:5 or SEQ ID NO:7 or nucleotides 503-564 of SEQ ID NO:3 and nucleotides 542-603 of SEQ ID NO:5 or SEQ ID NO:7. Polynucleotide probes of the invention can comprise a detectable label, such as a radioisotopic, fluorescent, enzymatic, or chemiluminescent label.

An hPNQALRE construct can be an expression construct which comprises a promoter which is functional in a selected host cell. The skilled artisan can readily select an appropriate promoter from the large number of cell type-specific promoters known and used in the art. The expression construct can also contain a transcription terminator which is functional in the host cell. The expression construct comprises a polynucleotide segment which encodes, for example, all or a portion of an hPNQALRE protein, variant, fusion protein, antibody, or ribozyme. The polynucleotide segment is located downstream from the promoter. Transcription of the polynucleotide segment initiates at the promoter.

A recombinant host cell comprising an hPNQALRE construct can be constructed, for example, to express all or a portion of an hPNQALRE protein. Preferred host cells express a portion of an hPNQALRE protein that comprises amino acids 26-38 of SEQ ID NO:6 or SEQ ID NO:8. Also preferred are host cells that express a portion of an hPNQALRE protein that comprises amino acids 181-201 of SEQ ID NO:6 or SEQ ID NO:8 as well as amino acids 168-188 of SEQ ID NO:4. Recombinant host cells comprising hPNQALRE expression constructs can be prokaryotic or eukaryotic. A variety of host cells are available for use in bacterial, yeast, insect, and human expression systems and can be used to express or to propagate hPNQALRE expression constructs.

Constructs can be introduced into host cells using any technique known in the art. These techniques include transferrin-polycation-mediated DNA transfer, transfection with naked or encapsulated nucleic acids, liposome-mediated cellular fusion, intracellular transportation of DNA-coated latex beads, protoplast fusion, viral infection, electroporation, and calcium phosphate-mediated transfection.

Bacterial systems for expressing hPNQALRE expression constructs include those described in Chang et al., *Nature* (1978) 275: 615, Goeddel et al., *Nature* (1979) 281: 544, Goeddel et al., *Nucleic Acids Res*. (1980)8: 4057, EP 36,776, U.S. Pat. No. 4,551,433, deBoer et al., *Proc. Natl. Acad. Sci. USA* (1983) 80: 21-25, and Siebenlist et al., *Cell* (1980) 20: 269.

Expression systems in yeast include those described in Hinnen et al., *Proc. Natl. Acad. Sci. USA* (1978) 75: 1929; Ito et al., *J. Bacteriol*. (1983) 153: 163; Kurtz et al., *Mol. Cell. Biol*. (1986) 6: 142; Kunze et al., *J. Basic Microbiol*. (1985) 25: 141; Gleeson et al., *J. Gen. Microbiol*. (1986) 132: 3459, Roggenkamp et al., *Mol. Gen. Genet*. (1986) 202: 302) Das et al., *J. Bacteriol*. (1984) 158: 1165; De Louvencourt et al., *J. Bacteriol*. (1983) 154: 737, Van den Berg et al., *Bio/Technology* (1990) 8: 135; Kunze et al., *J. Basic Microbiol*. (1985) 25: 141; Cregg et al., *Mol. Cell. Biol*. (1985) 5: 3376, U.S. Pat. No. 4,837,148, U.S. Pat. No. 4,929,555; Beach and Nurse, *Nature* (1981) 300: 706; Davidow et al., *Curr. Genet*. (1985) 10: 380, Gaillardin et al., *Curr. Genet*. (1985) 10: 49, Ballance et al., *Biochem. Biophys. Res. Commun*. (1983) 112: 284-289; Tilburn et al., *Gene* (1983) 26: 205-221, Yelton et al., *Proc. Natl. Acad. Sci. USA* (1984) 81: 1470-1474, Kelly and Hynes, *EMBO J*. (1985) 4: 475479; EP 244,234, and WO 91/00357.

Expression of hPNQALRE expression constructs in insects can be carried out as described in U.S. Pat. No. 4,745,051, Friesen et al. (1986) "The Regulation of Baculovirus Gene Expression" in: THE MOLECULAR BIOLOGY OF BACULOVIRUSES (W. Doerfler, ed.), EP 127,839, EP 155,476, and Vlak et al., *J. Gen. Virol*. (1988) 69: 765-776, Miller et al., *Ann. Rev. Microbiol*. (1988) 42: 177, Carbonell et al., *Gene* (1988) 73: 409, Maeda et al., *Nature* (1985) 315: 592-594, Lebacq-Verheyden et al., *Mol. Cell. Biol*. (1988) 8: 3129; Smith et al., *Proc. Natl. Acad. Sci. USA* (1985) 82: 8404, Miyajima et-al., *Gene* (1987) 58: 273, and Martin et al., *DNA* (1988) 7:99. Numerous baculoviral strains and variants and corresponding permissive insect host cells from hosts are described in Luckow et al., *Bio/Technology* (1988) 6: 47-55, Miller et al., in GENETC ENGINEERING (Setlow, J. K. et al. eds.), Vol. 8 (Plenum Publishing, 1986), pp. 277-279, and Maeda et al., *Nature*, (1985) 315: 592-594.

Mammalian expression of hPNQALRE expression constructs can be achieved as described in Dijkema et al., *EMBO J*. (1985) 4: 761, Gorman et al., *Proc. Natl. Acad. Sci. USA* (1982b) 79: 6777, Boshart et al., *Cell* (1985) 41: 521 and U.S. Pat. No. 4,399,216. Other features of mammalian expression of hPNQALRE expression constructs can be facilitated as described in Ham and Wallace, *Meth. Enz*. (1979) 58: 44, Barnes and Sato, *Anal. Biochem*. (1980) 102: 255, U.S. Pat. No. 4,767,704, U.S. Pat. No. 4,657,866, U.S. Pat. No. 4,927,762, U.S. Pat. No. 4,560,655, WO 90/103430, WO 87/00195, and U.S. RE 30,985.

Subgenomic polynucleotides of the invention can also be used in gene delivery vehicles, for the purpose of delivering an hPNQALRE mRNA or oligonucleotide (either with the sequence of native hPNQALRE mRNA or its complement), full-length hPNQALRE protein, hPNQALRE fusion protein, hPNQALRE polypeptide, biologically active or altered variant, or hPNQALRE-specific ribozyme or single-chain antibody into a cell, preferably a eukaryotic cell. According to the present invention, a gene delivery vehicle can be, for example, naked plasmid DNA, a viral expression vector comprising an hPNQALRE subgenomic polynucleotide, or an hPNQALRE subgenomic polynucleotide in conjunction with a liposome or a condensing agent.

In one embodiment of the invention, the gene delivery vehicle comprises a promoter and an hPNQALRE subgenomic polynucleotide. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter.

An hPNQALRE gene delivery vehicle can comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the hPNQALRE gene delivery vehicle is a recombinant retroviral vector. Recombinant retroviruses and various uses thereof have been described in numerous references including, for example, Mann et al., *Cell* 33:153, 1983, Cane and Mulligan, *Proc. Nat'l. Acad. Sci. USA* 81:6349, 1984, Miller et al., *Human Gene Therapy* 1:5-14, 1990, U.S. Pat. Nos. 4,405,712, 4,861,719, and 4,980,289, and PCT Application Nos. WO 89/02,468, WO 89/05,349, and WO 90/02,806.

Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, *Cancer Res.* 53:3860-3864, 1993; Vile and Hart, *Cancer Res.* 53:962-967, 1993; Ram et al., *Cancer Res.* 53:83-88, 1993; Takamiya et al., *J. Neurosci. Res.* 33:493-503, 1992; Baba et al., *J. Neurosurg.* 79:729-735, 1993 (U.S. Pat. No. 4,777,127, GB 2,200,651, EP 0,345,242 and WO 91/02805).

Particularly preferred retroviruses are derived from retroviruses which include avian leukosis virus (ATCC Nos. VR-535 and VR-247), bovine leukemia virus (VR-1315), murine leukemia virus (MLV), mink-cell focus-inducing virus (Koch et al., *J. Vir.* 49:828, 1984; and Oliff et al., *J. Vir.* 48:542, 1983), murine sarcoma virus (ATCC Nos. VR-844, 45010 and 45016), reticuloendotheliosis virus (ATCC Nos VR-994, VR-770 and 45011), Rous sarcoma virus, Mason-Pfizer monkey virus, baboon endogenous virus, endogenous feline retrovirus (e.g., RD114), and mouse or rat gL30 sequences used as a retroviral vector.

Particularly preferred strains of MLV from which recombinant retroviruses can be generated include 4070A and 1504A (Hartley and Rowe, *J. Vir.* 19:19, 1976), Abelson (ATCC No. VR-999), Friend (ATCC No. VR-245), Graffi (Ru et al., *J. Vir.* 67:4722, 1993; and Yantchev *Neoplasma* 26:397, 1979), Gross (ATCC No. VR-590), Kirsten (Albino et al., *J. Exp. Med.* 164:1710, 1986), Harvey sarcoma virus (Manly et al., *J. Vir.* 62:3540, 1988; and Albino et al., *J. Exp. Med.* 164:1710, 1986) and Rauscher (ATCC No. VR-998), and Moloney MLV (ATCC No. VR-190).

A particularly preferred non-mouse retrovirus is Rous sarcoma virus. Preferred Rous sarcoma viruses include Bratislava (Manly et al., *J. Vir.* 62:3540, 1988; and Albino et al., *J. Exp. Med.* 164:1710, 1986), Bryan high titer (e.g., ATCC Nos. VR-334, VR-657, VR-726, VR-659, and VR-728), Bryan standard (ATCC No. VR-140), Carr-Zilber (Adgighitov et al., *Neoplasma* 27:159, 1980), Engelbreth-Holm (Laurent et al., *Biochem Biophys Acta* 908:241, 1987), Harris, Prague (e.g., ATCC Nos. VR-772, and 45033), and Schmidt-Ruppin (e.g. ATCC Nos. VR-724, VR-725, VR-354) viruses.

Any of the above retroviruses can be readily utilized in order to assemble or construct retroviral hPNQALRE gene delivery vehicles given the disclosure provided herein and standard recombinant techniques (e.g., Sambrook et al., *Molecular Cloning: A Laboratory Manual*, 2d ed., Cold Spring Harbor Laboratory Press, 1989, and Kunkle, *PNAS* 82:488, 1985) known in the art. Portions of retroviral hPN-QALRE expression vectors can be derived from different retroviruses. For example, retrovector LTRs can be derived from a murine sarcoma virus, a tRNA binding site from a Rous sarcoma virus, a packaging signal from a murine leukemia virus, and an origin of second strand synthesis from an avian leukosis virus.

Recombinant retroviral vectors can be used to generate transduction competent retroviral vector particles by introducing them into appropriate packaging cell lines (see Ser. No. 07/800,921, filed Nov. 29, 1991). Recombinant retroviruses can be produced which direct the site-specific integration of the recombinant retroviral genome into specific regions of the host cell DNA. Site-specific integration can be mediated by a chimeric integrase incorporated into the retroviral particle (see Ser. No. 08/445,466 filed May 22, 1995). It is preferable that the recombinant viral gene delivery vehicle is a replication-defective recombinant virus.

Packaging cell lines suitable for use with the above-described retroviral gene delivery vehicles can be readily prepared (see Ser. No. 08/240,030, filed May 9, 1994; see also WO 92/05266) and used to create producer cell lines (also termed vector cell lines or "VCLs") for production of recombinant viral particles. In particularly preferred embodiments of the present invention, packaging cell lines are made from human (e.g., HT1080 cells) or mink parent cell lines, thereby allowing production of recombinant retroviral gene delivery vehicles which are capable of surviving inactivation in human serum. The construction of recombinant retroviral gene delivery vehicles is described in detail in WO 91/02805.

Recombinant retroviral gene delivery vehicles can be used to generate transduction competent retroviral particles by introducing them into appropriate packaging cell lines (see Ser. No. 07/800,921). Similarly, adenovirus gene delivery vehicles can also be readily prepared and utilized given the disclosure provided herein (see also Berkner, *Biotechniques* 6:616-627, 1988, and Rosenfeld et al., *Science* 252:431-434, 1991, WO 93/07283, WO 93/06223, and WO 93/07282).

An hPNQALRE gene delivery vehicle can also be a recombinant adenoviral gene delivery vehicle. Such vehicles can be readily prepared and utilized given the disclosure provided herein (see Berkner, *Biotechniques* 6:616, 1988, and Rosenfeld et al., *Science* 252:431, 1991, WO 93/07283, WO 93/06223, and WO 93/07282). Adeno-associated viral hPNQALRE gene delivery vehicles can also be constructed and used to deliver hPNQALRE amino acids or nucleotides.

The use of adeno-associated viral gene delivery vehicles in vitro is described in Chatterjee et al., *Science* 258: 1485-1488 (1992), Walsh et al., *Proc. Nat'l. Acad. Sci.* 89: 7257-7261 (1992), Walsh et al., *J. Clin. Invest.* 94: 1440-1448 (1994), Flotte et al., *J. Biol. Chem.* 268: 3781-3790 (1993), Ponnazhagan et al., *J. Exp. Med.* 179: 733-738 (1994), Miller et al., *Proc. Nat'l Acad. Sci.* 91: 10183-10187 (1994), Einerhand et al., *Gene Ther.* 2: 336-343 (1995), Luo et al., *Exp. Hematol.* 23: 1261-1267 (1995), and Zhou et al., *Gene Therapy* 3: 223-229 (1996). In vivo use of these vehicles is described in Flotte et al., *Proc. Nat'l Acad. Sci.* 90: 10613-10617 (1993), and Kaplitt et al., *Nature Genet.* 8:148-153 (1994).

In another embodiment of the invention, an hPNQALRE gene delivery vehicle is derived from a togavirus. Preferred togaviruses include alphaviruses, in particular those described in U.S. Ser. No. 08/405,627, filed Mar. 15, 1995, WO 95/07994. Alpha viruses, including Sindbis and ELVS viruses can be gene delivery vehicles for hPNQALRE polynucleotides. Alpha viruses are described in WO 94/21792, WO 92/10578 and WO 95/07994. Several different alphavirus gene delivery vehicle systems can be constructed and used to deliver hPNQALRE subgenomic polynucleotides to a cell according to the present invention. Representative examples of such systems include those described in U.S. Pat. Nos. 5,091,309 and 5,217,879. Particularly preferred alphavirus gene delivery vehicles for use in the present invention include those which are described in WO 95/07994, and U.S. Ser. No. 08/405,627.

Preferably, the recombinant viral vehicle is a recombinant alphavirus viral vehicle based on a Sindbis virus. Sindbis constructs, as well as numerous similar constructs, can be readily prepared essentially as described in U.S. Ser. No. 08/198,450. Sindbis viral gene delivery vehicles typically comprise a 5' sequence capable of initiating Sindbis virus transcription, a nucleotide sequence encoding Sindbis nonstructural proteins, a viral junction region inactivated so as to prevent subgenomic fragment transcription, and a Sindbis RNA polymerase recognition sequence. Optionally, the viral junction region can be modified so that subgenomic polynucleotide transcription is reduced, increased, or maintained. As will be appreciated by those in; the art, corresponding regions from other alphaviruses can be used in place of those described above.

The viral junction region of an alphavirus-derived gene delivery vehicle can comprise a first viral junction region which has been inactivated in order to prevent transcription of the subgenomic polynucleotide and a second viral junction region which has been modified such that subgenomic polynucleotide transcription is reduced. An alphavirus-derived vehicle can also include a 5' promoter capable of initiating synthesis of viral RNA from cDNA and a 3' sequence which controls transcription termination.

Other recombinant togaviral gene delivery vehicles which can be utilized in the present invention include those derived from Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309 and 5,217,879 and in WO 92/10578. The Sindbis vehicles described above, as well as numerous similar constructs, can be readily prepared essentially as described in U.S. Ser. No. 08/198,450.

Other viral gene delivery vehicles suitable for use in the present invention include, for example, those derived from poliovirus (Evans et al., *Nature* 339:385, 1989, and Sabin et al., *J. Biol. Standardization* 1:115, 1973) (ATCC VR-58); rhinovirus (Arnold et al., *J. Cell. Biochem.* L401, 1990) (ATCC VR-1110); pox viruses, such as canary pox virus or vaccinia virus (Fisher-Hoch et al., *PNAS* 86:317, 1989; Flexner et al., *Ann. N.Y. Acad. Sci.* 569:86, 1989; Flexner et al., *Vaccine* 8:17, 1990; U.S. Pat. No. 4,603,112 and U.S. Pat. No. 4,769,330; WO 89/01973) (ATCC VR-111; ATCC VR-2010); SV40 (Mulligan et al., *Nature* 277:108, 1979) (ATCC VR-305), (Madzak et al., *J. Gen. Vir.* 73:1533, 1992); and influenza virus (Luytjes et al., *Cell* 59:1107, 1989; McMicheal et al., *The New England Journal of Medicine* 309:13, 1983; and Yap et al., *Nature* 273:238, 1978) (ATCC VR-797).

Other viruses which can be used to derive gene delivery vehicles include parvoviruses such as adeno-associated virus (Samulski et al., *J. Vir.* 63:3822, 1989, and Mendelson et al., *Virology* 166:154, 1988) (ATCC VR-645); herpes simplex virus (Kit et al., *Adv. Exp. Med. Biol.* 215:219, 1989) (ATCC VR-977; ATCC VR-260); *Nature* 277:108, 1979); human immunodeficiency virus (EPO 386,882, Buchschacher et al., *J. Vir.* 66:2731, 1992); and measles virus (EPO 440,219) (ATCC VR-24); A (ATCC VR-67; ATCC VR-1247).

Aura (ATCC VR-368), Bebaru virus (ATCC VR-600; ATCC VR-1240), Cabassou (ATCC VR-922), Chikungunya virus (ATCC VR-64; ATCC VR-1241), Fort Morgan (ATCC VR-924), Getah virus (ATCC VR-369; ATCC VR-1243), Kyzylagach (ATCC VR-927), Mayaro (ATCC VR-66), Mucambo virus (ATCC VR-580; ATCC VR-1244), Ndumu (ATCC VR-371), Pixuna virus (ATCC VR-372; ATCC VR-1245), Tonate (ATCC VR-925), Triniti (ATCC VR-469), Una (ATCC VR-374), Whataroa (ATCC VR-926), Y-62-33 (ATCC VR-375), O'Nyong virus, Eastern encephalitis virus (ATCC VR-65; ATCC VR-1242), Western encephalitis virus (ATCC VR-70; ATCC VR-1251; ATCC VR-622; ATCC VR-1252), and coronavirus (Hamre et al., *Proc. Soc. Exp. Biol. Med.* 121:190, 1966) (ATCC VR-740) can also be used to provide gene delivery vehicles.

An hPNQALRE subgenomic polynucleotide of the invention can be combined with a condensing agent to form a gene delivery vehicle. In a preferred embodiment, the condensing agent is a polycation, such as polylysine, polyarginine, polyornithine, protamine, spermine, spermidine, and putrescine. Many suitable methods for making such linkages are known in the art (see, for example, Ser. No. 08/366,787, filed Dec. 30, 1994).

Alternatively, an hPNQALRE subgenomic polynucleotide can be with a liposome to form a gene delivery vehicle. Liposomes are small, lipid vesicles comprised of an aqueous compartment enclosed by a lipid bilayer, typically spherical or slightly elongated structures several hundred Angstroms in diameter. Under appropriate conditions, a liposome can fuse with the plasma membrane of a cell or with the membrane of an endocytic vesicle within a cell which has internalized the liposome, thereby releasing its contents into the cytoplasm. Prior to interaction with the surface of a cell, however, the liposome membrane acts as a relatively impermeable barrier which sequesters and protects its contents, for example, from degradative enzymes.

Additionally, because a liposome is a synthetic structure, specially designed liposomes can be produced which incorporate desirable features. See Stryer, *Biochemistry*, pp. 236-240, 1975 (W.H. Freeman, San Francisco, Calif.); Szoka et al., *Biochim. Biophys. Acta* 600:1, 1980; Bayer et al., *Biochim. Biophys. Acta.* 550:464, 1979; Rivnay et al., *Meth. Enzylnol.* 149:119, 1987; Wang et al., *PNAS* 84: 7851, 1987, Plant et al., *Anal. Biochem.* 176:420, 1989, and U.S. Pat. No. 4,762,915. Liposomes can encapsulate a variety of nucleic acid molecules including DNA, RNA, plasmids, and expression constructs comprising hPNQALRE subgenomic polynucleotides such those disclosed in the present invention.

Liposomal preparations for use in the present invention include cationic (positively charged), anionic (negatively charged) and neutral preparations. Cationic liposomes have been shown to mediate intracellular delivery of plasmid DNA (Felgner et al., *Proc. Natl. Acad. Sci. USA* 84:7413-7416, 1987), mRNA (Malone et al., *Proc. Natl. Acad. Sci. USA* 86:6077-6081, 1989), and purified transcription factors (Debs et al., *J. Biol. Chem.* 265:10189-10192, 1990), in functional form. Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. See also Felgner et al., *Proc. Natl. Acad. Sci. USA* 91: 5148-5152.87, 1994.

Other commercially available liposomes include Transfectace (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* 75:4194-4198, 1978; and WO 90/11092 for descriptions of the synthesis of DOTAP (1,2-bis(oleoyloxy)-3-(trimethylammonio)propane) liposomes.

Similarly, anionic and neutral liposomes are readily available, such as from Avanti Polar. Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., METHODS OF IMMUNOLOGY (1983), Vol. 101, pp. 512-527; Szoka et al., Proc. Natl. Acad. Sci. USA 87:3410-3414, 1990; Papahadjopoulos et al., Biochim. Biophys. Acta 394:483, 1975; Wilson et al., Cell 17:77, 1979; Deamer and Bangham, Biochim. Biophys. Acta 443:629, 1976; Ostro et al., Biochem. Biophys. Res. Commun. 76:836, 1977; Fraley et al., Proc. Natl. Acad. Sci. USA 76:3348, 1979; Enoch and Strittmatter, Proc. Nat. Acad. Sci. USA 76:145, 1979; Fraley et al., J. Biol. Chem. 255:10431, 1980; Szoka and Papahadjopoulos, Proc. Natl. Acad. Sci. USA 75:145, 1979; and Schaefer-Ridder et al., Science 215:166, 1982.

In addition, lipoproteins can be included with an hPNQALRE subgenomic polynucleotide for delivery to a cell. Examples of such lipoproteins include chylomicrons, HDL, IDL, LDL, and VLDL. Mutants, fragments, or fusions of these proteins can also be used. Modifications of naturally occurring lipoproteins can also be used, such as acetylated LDL. These lipoproteins can target the delivery of polynucleotides to cells expressing lipoprotein receptors. Preferably, if lipoproteins are included with a polynucleotide, no other targeting ligand is included in the composition.

"Naked" hPNQALRE subgenomic polynucleotide molecules can also be used as gene delivery vehicles, as described in WO 90/11092 and U.S. Pat. No. 5,580,859. Such gene delivery vehicles can be either hPNQALRE DNA or RNA and, in certain embodiments, are linked to killed adenovirus. Curiel et al., Hum. Gene. Ther. 3:147-154, 1992. Other suitable vehicles include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad Sci. 88:2726-2730, 1991).

The efficiency of naked hPNQALRE subgenomic polynucleotide uptake into cells can be increased by coating the polynucleotides onto biodegradable latex beads, which are efficiently transported and concentrated in the perinuclear region of the cells. hPNQALRE subgenomic polynucleotide-coated latex beads can be injected into cells and will be efficiently transported into cells after the beads initiate endocytosis, thus increasing gene transfer and expression efficiency. This method can be improved further by treating the beads to increase their hydrophobicity, thereby facilitating the disruption of the endosome and release of hPNQALRE subgenomic polynucleotides into the cytoplasm.

hPNQALRE may interact with different cyclins to achieve different effects within a cell. For example, cyclins which bind to hPNQALRE may function to regulate transcription. Cyclins which bind to hPNQALRE can be identified using screens such as the yeast two-hybrid assay. This assay is described inter alia in Fields & Song, *Nature* 340:245-46, 1989.

hPNQALRE mRNA is over-expressed in tumors compared with hPNQALRE mRNA expression levels in normal tissue. According to the present invention, tumors can be treated by contacting the tumor with a composition which can decrease the level of functional hPNQALRE protein in the tumor, for example, by decreasing levels of hPNQALRE or by blocking or reducing its function. Neoplasias which can be treated include, but are not limited to, colorectal carcinomas, melanomas, squamous cell carcinomas, adenocarcinomas, hepatocellular carcinomas, renal cell carcinomas, sarcomas, myosarcomas, non-small cell lung carcinomas, leukemias, lymphomas, osteosarcomas, central nervous system tumors such as gliomas, astrocytomas, oligodendrogliomas, and neuroblastomas, breast tumors, tumors of mixed origin, such as Wilms' tumor and teratocarcinomas, and metastatic tumors. Proliferative disorders, such as anhydric hereditary ectodermal dysplasia, congenital alveolar dysplasia, epithelial dysplasia of the cervix, fibrous dysplasia of bone, and mammary dysplasia, can also be treated according to the invention. Hyperplasias, for example, endometrial, adrenal, breast, prostate, or thyroid hyperplasias, or pseudoepitheliomatous hyperplasia of the skin can also be treated according to the present invention.

The composition comprises a reagent which specifically binds to an hPNQALRE expression product so as to decrease the level of functional hPNQALRE protein in a cell, such as a tumor cell. In one embodiment of the invention, the reagent is a ribozyme, an RNA molecule with catalytic activity. See, e.g., Cech, *Science* 236: 1532-1539; 1987; Cech, *Ann. Rev. Biochem.* 59:543-568; 1990, Cech, *Curr. Opin. Struct. Biol.* 2: 605-609; 1992, Couture and Stinchcomb, *Trends Genet.* 12: 510-515, 1996. Ribozyrnes can be used to inhibit gene function by cleaving an RNA sequence, as is known in the art (e.g., Haseloff et al., U.S. Pat. No. 5,641,673).

A coding sequence of an hPNQALRE gene can be used to generate ribozymes which will specifically bind to mRNA transcribed from the hPNQALRE gene. Methods of designing and constructing ribozymes which can cleave other RNA molecules in trans in a highly sequence specific manner have been developed and described in the art (see Haseloff et al. *Nature* 334:585-591, 1988). For example, the cleavage activity of ribozymes can be targeted to specific hPNQALRE RNAs by engineering a discrete "hybridization" region into the ribozyme. The hybridization region contains a sequence complementary to the target hPNQALRE RNA and thus specifically hybridizes with the target (see, for example, Gerlach et al., EP 321,201). The nucleotide sequences shown in SEQ ID NOS:1, 3, 5, and 7 provide sources of suitable hybridization region sequences. Preferred ribozyme "hybridization" regions comprise in whole or in part nucleotides 76-114 of SEQ ID NO:5 or SEQ ID NO:7. Other preferred ribozyme "hybridization" regions comprise in whole or in part nucleotides 503-564 of SEQ ID NO:3 or nucleotides 542-603 of SEQ ID NO:5 or SEQ ID NO:7. Longer complementary sequences can be used to increase the affinity of the hybridization sequence for the target. The hybridizing and cleavage regions of the hPNQALPE ribozyme can be integrally related; thus, upon hybridizing to the target hPNQALRE RNA through the complementary regions, the catalytic region of the ribozyme can cleave the target.

hPNQALRE ribozymes can be introduced into cells as part of a construct, as is known in the art and described above. Mechanical methods, such as microinjection, liposome-mediated transfection, electroporation, or calcium phosphate precipitation, can be used to introduce the ribozyme-containing construct into cells in which it is desired to decrease hPNQALRE expression, as described above. Alternatively, if it is desired that the cells stably retain the construct, it can be supplied on a plasmid and maintained as a separate element or integrated into the genome of the cells, as is known in the art. The construct can include transcriptional regulatory elements, such as a promoter element, an enhancer or UAS element, and a transcriptional terminator signal, for controlling transcription of hPNQALRE ribozymes in the cells.

In another embodiment of the invention, the level of hPNQALRE protein is decreased using an antisense oligonucleotide sequence. The antisense sequence is complementary to at least a portion of a sequence encoding hPNQALRE selected from the nucleotide sequences shown in SEQ ID NOS:1, 3, 5, and 7. Preferably, the antisense oligonucleotide sequence is at least 11 nucleotides in length, but can be at least 12, 15, 20, 25, 30, 35, 40, 45, or 50 or more nucleotides long. More preferably, antisense oligonucleotide sequences of 11, 12, 15, 20, 25, 30, 35, 40, 45, or 50 or more nucleotides are complementary to nucleotides 76-114 of SEQ ID NO:5 and SEQ ID NO:7 or are complementary to nucleotides 503-564 of SEQ ID NO:3 or nucleotides 542-603 of SEQ ID NO:5 or SEQ ID NO:7. Longer sequences can also be used. hPNQALRE antisense oligonucleotide molecules can be provided in a construct and introduced into cells as disclosed herein to decrease the level of functional hPNQALRE protein in the cells.

hPNQALRE anti sense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20:1-8, 1994; Sonveaux, *Meth. Mol. Biol.* 26:1-72, 1994; Uhlmann et al., *Chem. Rev.* 90:543-583, 1990.

Precise complementarity is not required for successful duplex formation between an antisense molecule and the complementary coding sequence of an hPNQALRE gene. Antisense molecules which comprise, for example, 2, 3, 4, or 5 or more stretches of contiguous nucleotides which are precisely complementary to an hPNQALRE coding sequence, each separated by a stretch of contiguous nucleotides which are not complementary to adjacent hPNQALRE coding sequences, can provide targeting specificity for hPNQALRE mRNA. Preferably, each stretch of contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular hPNQALRE coding sequence.

hPNQALRE antisense oligonucleotides can be modified without affecting their ability to hybridize to an hPNQALRE coding sequence. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3',5'-substituted oligonucleotide in which the 3' hydroxyl group or the 5' phosphate group are substituted, can also be employed in a modified antisense oligonucleotide. These modified oligonucleotides can be prepared by methods well known in the art. See, e.g., Agrawal et al., *Trends Biotechnol.* 10:152-158, 1992; Uhlmarn et al., *Chem. Rev.* 90:543-584, 1990; Uhlmann et al., *Tetrahedron. Lett.* 215:3539-3542, 1987.

Antibodies of the invention which specifically bind to hPNQALRE epitopes, particularly to the cyclin binding domain of hPNQALRE, can also be used to alter levels of functional hPNQALRE protein, by binding to hPNQALRE protein and decreasing the level of hPNQALRE protein which can function in the cell. Polynucleotides encoding single-chain antibodies of the invention can be introduced into cells as described above.

Preferably, the mechanism used to decrease the level of functional hPNQALRE in a cell decreases the level of functional hPNQALRE protein by at least 50%, 60%, 70%, or 80%. Most preferably, the level of functional hPNQALRE protein is decreased by at least 90%, 95%, 99%, or 100%. The effectiveness of the mechanism chosen to decrease the level of functional hPNQALRE protein can be assessed using methods well known in the art, such as hybridization of nucleotide probes to hPNQALRE mRNA, quantitative RT-PCR, detection of hPNQALRE protein using hPNQALRE-specific antibodies of the invention, or measurement of cyclin-dependent kinase activity. Assays for cyclin-dependent kinase activity are taught, for example, in Lock et al., 1997, *Cancer Chemother. Pharmacol.* 39:399-409.

Compositions comprising hPNQALRE antibodies, ribozymes, or antisense oligonucleotides can optionally comprise a pharmaceutically acceptable carrier. Pharmaceutically acceptable carriers are well known to those in the art. Such carriers include, but are not limited to, large, slowly metabolized macromolecules, such as proteins, polysaccharides, polylactic acids, polyglycolic acids, polymeric amino acids, amino acid copolymers, and inactive virus particles. Pharmaceutically acceptable salts can also be used in hPNQALRE compositions, for example, mineral salts such as hydrochlorides, hydrobromides, phosphates, or sulfates, as well as salts of organic acids such as acetates, proprionates, malonates, or benzoates. hPNQALRE compositions can also contain liquids, such as water, saline, glycerol, and ethanol, as well as substances such as wetting agents, emulsifying agents, or pH buffering agents. Liposomes, such as those described in U.S. Pat. No. 5,422,120, WO 95/13796, WO 91/14445, or EP 524,968 B1, can also be used as a carrier for an hPNQALRE composition.

Typically, an hPNQALRE composition is prepared as an injectable, either as a liquid solution or suspension; however, solid forms suitable for solution or suspension in liquid vehicles prior to injection can also be prepared. An hPNQALRE composition can also be formulated into an enteric coated tablet or gel capsule according to known methods in the art, such as those described in U.S. Pat. No. 4,853,230, EP 225,189, AU 9,224,296, and AU 9,230,801.

Administration of hPNQALRE compositions of the invention can include local or systemic administration, including injection, oral administration, particle gun, or catheterized administration, and topical administration. Various methods can be used to administer an hPNQALRE composition directly to a specific site in the body. For inducing apoptosis in a tumor, for example, an appropriate hPNQALRE composition injected several times in several different locations within the body of the tumor. Alternatively, arteries which serve the tumor can be identified, and an hPNQALRE composition can be injected into such an artery in order to deliver the composition to the tumor.

A tumor which has a necrotic center can be aspirated, and an hPNQALRE composition can be injected directly into the now empty center of the tumor. An hPNQALRE composition can also be administered directly to the surface of a tumor, for example, by topical application of the composition. X-ray imaging can be used to assist in certain of these delivery methods. Combination therapeutic agents, including an hPNQALRE-specific antibody, ribozyme, or oligonucleotide or a subgenomic hPNQALRE polynucleotide encoding an hPNQALRE-specific antibody, ribozyme, or oligonucleotide, can be administered simultaneously or sequentially together with other therapeutic agents.

hPNQALRE compositions can be delivered to specific tissues using receptor-mediated targeted delivery. Receptor-mediated DNA delivery techniques are taught in, for example, Findeis et al. *Trends in Biotechnol.* 11, 202-05, (1993); Chiou et al., GENE THERAPEUTICS: METHODS AND APPLICATIONS OF DIRECT GENE TRANSFER (J. A. Wolff, ed.) (1994); Wu & Wu, *J. Biol. Chem.* 263, 621-24, 1988; Wu et al., *J. Biol. Chem.* 269, 542-46, 1994; Zenke et al., *Proc. Natl. Acad. Sci. U.S.A.* 87, 3655-59, 1990; Wu et al., *J. Biol. Chem.* 266, 338-42, 1991.

Both the dose of a particular hPNQALRE composition and the means of administering the composition can be determined based on specific qualities of the hPNQALRE composition, the condition, age, and weight of the patient, the progression of the particular disease being treated, and other relevant factors. If the composition contains hPNQALRE antibodies, effective dosages of the composition are in the range of about 5 µg to about 50 mg/kg of patient body weight, about 50 µg to about 5 mg/kg, about 100 µg to about 500 µg/kg of patient body weight, and about 200 to about 250 µg/kg.

Compositions containing hPNQALRE subgenomic polynucleotides, including antisense oligonucleotides and ribozyme- or antibody-encoding sequences, can be administered in a range of about 100 ng to about 200 mg of DNA for local administration. Suitable concentrations range from about 500 ng to about 50 mg, about 1 µg to about 2 mg, about 5 µg to about 500 µg, and about 20 µg to about 100 µg of DNA. Factors such as method of action and efficacy of transformation and expression are considerations which will affect the dosage required for ultimate efficacy of the hPNQALRE composition. If greater expression is desired over a larger area of tissue, larger amounts of an hPNQALRE composition or the same amount administered successively, or several administrations to different adjacent or close tissue portions of, for example, a tumor site, may be required to effect a positive therapeutic outcome. In all cases, routine experimentation in clinical trials will determine specific ranges for optimal therapeutic effect.

Expression of an endogenous hPNQALRE gene in a cell can be altered by introducing in frame with the endogenous hPNQALRE gene a DNA construct comprising an hPNQALRE targeting sequence, a regulatory sequence, an exon, and an unpaired splice donor site by homologous recombination, such that a homologously recombinant cell comprising a new hPNQALRE transcription unit is formed. The new transcription unit can be used to turn the hPNQALRE gene on or off as desired. This method of affecting endogenous gene expression is taught in U.S. Pat. No. 5,641,670.

The targeting sequence is a segment of at least 10, 12, 15, 20, or 50 contiguous nucleotides selected from a nucleotide sequence shown in SEQ ID NOS:1, 3, 5, or 7. Preferred targeting sequences are selected from nucleotides 76-114 of SEQ ID NO:5 and SEQ ID NO:7 as well as from nucleotides 503-564 of SEQ ID NO:3 or nucleotides 542-603 of SEQ ID NO:5 or SEQ ID NO:7. The new transcription unit is located upstream of a coding sequence of the endogenous hPNQALRE gene. The exogenous regulatory sequence directs transcription of the coding sequence of the hPNQALRE gene.

The invention also provides a method of diagnosing or prognosing neoplasia in a mammal, preferably a human. Expression of an hPNQALRE gene in a first tissue suspected of being neoplastic can be compared with expression of an hPNQALRE gene in a second tissue which is normal. The hPNQALRE gene can have a coding sequence as shown in SEQ ID NOS:1, 3, 5, or 7. Preferably, the hPNQALRE gene will comprise nucleotides 76-114 of SEQ ID NO:5 and SEQ ID NO:7 and/or nucleotides 503-564 of SEQ ID NO:3 or nucleotides 542-603 of SEQ ID NO:5 or SEQ ID NO:7.

Comparisons can be made, for example, by measuring levels of hPNQALRE mRNA or hPNQALRE protein in the first and second tissues, as is known in the art. The first and second tissues can originate from the same subject or from different subjects. The first and second tissues can be of different types, but are preferably from the same type of tissue, such as an intestinal polyp. Alternatively, standard curves of hPNQALRE gene expression can be determined from a number of normal tissue samples and used for comparison with hPNQALRE gene expression in a tissue suspected of being neoplastic.

Over-expression of the hPNQALRE gene in the first tissue compared with hPNQALRE gene expression in the second tissue or the standard curve indicates neoplasia in the first tissue. Levels of over-expression can correlate with stages of neoplasia and can be used, for example, to monitor treatment of a patient, preferably a human patient.

An hPNQALRE subgenomic polynucleotide can also be delivered to subjects for the purpose of screening test compounds for those which are useful for enhancing transfer of hPNQALRE subgenomic polynucleotides to the cell or for enhancing subsequent biological effects of hPNQALRE subgenomic polynucleotides within the cell. Such biological effects include hybridization to complementary hPNQALRE mRNA and inhibition of its translation, expression of an hPNQALRE subgenomic polynucleotide to form an hPNQALRE mRNA, single-chain antibody, ribozyme, oligonucleotide, or protein and/or hPNQALRE and replication and integration of an hPNQALRE subgenomic polynucleotide. The subject can be a cell culture or an animal, preferably a mammal, more preferably a human.

Test compounds which can be screened include any substances, whether natural products or synthetic, which can be administered to the subject in vitro or in vivo. Libraries or mixtures of compounds can be tested. The compounds or substances can be those for which a pharmaceutical effect is previously known or unknown. The compounds or substances can be delivered before, after, or concomitantly with an hPNQALRE subgenomic polynucleotide. They can be administered separately or in admixture with an hPNQALRE subgenomic polynucleotide.

Integration of a delivered hPNQALRE subgenomic polynucleotide can be monitored by any means known in the art. For example, Southern blotting of the delivered hPNQALRE subgenomic polynucleotide can be performed. A change in the size of the fragments of a delivered polynucleotide indicates integration. Replication of a delivered polynucleotide can be monitored inter alia by detecting incorporation of labeled nucleotides combined with hybridization to an hPNQALRE probe. Expression of an hPNQALRE subgenomic polynucleotide can be monitored by detecting production of hPNQALRE mRNA which hybridizes to the delivered polynucleotide or by detecting hPNQALRE protein. hPNQALRE protein can be detected immunologically. Thus, the delivery of hPNQALRE subgenomic polynucleotides according to the present invention provides an excellent system for screening test compounds for their ability to enhance transfer of hPNQALRE polynucleotides to a cell, by enhancing delivery, integration, hybridization, expression, replication or integration in a cell in vitro or in vivo in an animal, preferably a mammal, more preferably a human.

The complete contents of all references cited in this disclosure are expressly incorporated by reference herein. The following are provided for exemplification purposes only and are not intended to limit the scope of the invention which has been described in broad terms above.

EXAMPLES

This example demonstrates expression of hPNQALRE mRNA in human tissues and cell lines.

Northern blots of human heart, brain, placenta, lung, liver, muscle, kidney, pancreas, spleen, thymus, prostate, testis, ovary, small intestine, colon and peripheral blood lymphocytes were assayed for hPNQALRE expression. The cell lines HL-60, HeLa, Molt-4, K565, Raji, SW480, A549, and G361 were also assayed for hPNQALRE mRNA expression.

hPNQALRE mRNA is expressed in most tissues at very low levels. Expression was most pronounced in brain, pancreas, testis, and ovary. In contrast, hPNQALRE mRNA was expressed at higher levels in cancer cell lines. Expression of hPNQALRE mRNA was highest in the cell lines K565, A549, G361, and SW480.

These results indicate that hPNQALRE is over-expressed in cancer cell lines compared with expression levels in the corresponding normal tissues.

Example 2

This example describes distribution of hPNQALRE mRNA in developing mouse embryos.

Mouse embryos were processed for whole-mount in situ hybridization as described in Lyn, S. D., "Whole-mount in situ hybridization of mouse embryos exposed to teratogenic levels of retinoic acid," *Meth. Mol. Biol.*, 89:67-69, 1998, and Nieto et al., "In situ hybridization analysis of chick embryos in whole mount and tissue sections," *Meth. Cell Biol.*, 51:219-35, 1996. In situ hybridization on whole mount embryos indicated that hPNQALRE mRNA is expressed overall in embryonic tissue, particularly in the developing limbs.

These results indicate that hPNQALRE may become differentially expressed in particular tissues over the course of embryonic development.

Example 3

This example demonstrates the generation of polyclonal antibodies against hPNQALRE.

Rabbits were immunized with a peptide fragment of hPNQALRE with the sequence N-HDFHVDRPLEESLINPE-LIRP-C (SEQ ID NO:17) coupled to keyhole limpet hemocyanin. A preparation of polyclonal antibodies was generated which recognized hPNQALRE protein expressed from COS and U87 cells.

These results demonstrate that hPNQALRE polypeptide fragments can be used as immunogens.

Those skilled in the art will recognize, or be able to ascertain, using not more than routine experimentation, many equivalents to the specific embodiments of the invention described herein. Such specific embodiments and equivalents are intended to be encompassed by the following claims.

All patents, published patent applications, and publications cited herein are incorporated by reference as if set forth fully herein.

What is claimed is:

1. An isolated polypeptide comprising the amino acid sequence of SEQ ID NO: 2.

2. An isolated polypeptide comprising at least 223 contiguous amino acids of the amino acid sequence of SEQ ID NO: 2.

3. A fusion protein comprising a first protein segment and a second protein segment, said first protein segment fused to said second protein segment by means of a peptide bond, wherein said first protein segment comprises the amino acid sequence of SEQ ID NO: 2.

4. An isolated polypeptide encoded by the nucleotide sequence of SEQ ID NO: 1.

* * * * *

SEQUENCE LISTING

<160> NUMBER OF SEQ ID NOS: 17

<210> SEQ ID NO 1
<211> LENGTH: 1002
<212> TYPE: DNA
<213> ORGANISM: Homo sapien

<400> SEQUENCE: 1

```
ggaccttcta gaatggacca gtactgcatc ctgggccgca tcggggaggg cgcccacggc      60
atcgtcttca aggccaagca cgtggagact ggcgagatag ttgccctcaa gaaggtggcc     120
ctaaggcggt tggaagacgg cttccctaac caggccctgc gggagattaa ggctctgcag     180
gagatggagg acaatcagta tgtggtacaa ctgaaggctg tgttcccaca cggtggaggc     240
tttgtgctgg cctttgagtt catgctgtcg gatctggccg aggtggtgcg ccatgcccag     300
aggccactag cccaggcaca ggtcaagagc tacctgcaga tgctgctcaa gggtgtcgcc     360
ttctgccatg ccaacaacat tgtacatcgg gacctgaaac ctgccaacct gctcatcagc     420
gcctcaggcc agctcaagat agcggacttt ggcctggctc gagtcttttc cccagacggc     480
agccgcctct acacacacca ggtggccacc aggtctgtgg gctgcatcat gggggagctg     540
ttgaatgggt ccccccttt cccgggcaag aacgatattg aacagctttg ctatgtgctt     600
cgcatcttgg gcaccccaaa ccctcaagtc tggccggagc tcactgagct gccggactac     660
aacaagatct cccttaagga gcaggtgccc atgcccctgg aggaggtgct gcctgacgtc     720
tctccccagg cattggatct gctgggtcaa ttccttctct accctcctca ccagcgcatc     780
gcagcttcca aggctctcct ccatcagtac ttcttcacag ctcccctgcc tgcccatcca     840
tctgagctgc cgattcctca gcgtctaggg ggacctgccc ccaaggccca tccagggccc     900
```

```
cccacatcc atgacttcca cgtggaccgg cctcttgagg agtcgctgtt gaacccagag      960
ctgattcggc ccttcatcct ggagaggtga ggatcctgag aa                       1002
```

<210> SEQ ID NO 2
<211> LENGTH: 325
<212> TYPE: PRT
<213> ORGANISM: Homo sapien

<400> SEQUENCE: 2

```
Met Asp Gln Tyr Cys Ile Leu Gly Arg Ile Gly Glu Gly Ala His Gly
 1               5                  10                  15

Ile Val Phe Lys Ala Lys His Val Glu Thr Gly Glu Ile Val Ala Leu
            20                  25                  30

Lys Lys Val Ala Leu Arg Arg Leu Glu Asp Gly Phe Pro Asn Gln Ala
        35                  40                  45

Leu Arg Glu Ile Lys Ala Leu Gln Glu Met Glu Asp Asn Gln Tyr Val
    50                  55                  60

Val Gln Leu Lys Ala Val Phe Pro His Gly Gly Gly Phe Val Leu Ala
65                  70                  75                  80

Phe Glu Phe Met Leu Ser Asp Leu Ala Glu Val Val Arg His Ala Gln
                85                  90                  95

Arg Pro Leu Ala Gln Ala Gln Val Lys Ser Tyr Leu Gln Met Leu Leu
            100                 105                 110

Lys Gly Val Ala Phe Cys His Ala Asn Asn Ile Val His Arg Asp Leu
        115                 120                 125

Lys Pro Ala Asn Leu Leu Ile Ser Ala Ser Gly Gln Leu Lys Ile Ala
    130                 135                 140

Asp Phe Gly Leu Ala Arg Val Phe Ser Pro Asp Gly Ser Arg Leu Tyr
145                 150                 155                 160

Thr His Gln Val Ala Thr Arg Ser Val Gly Cys Ile Met Gly Glu Leu
                165                 170                 175

Leu Asn Gly Ser Pro Leu Phe Pro Gly Lys Asn Asp Ile Glu Gln Leu
            180                 185                 190

Cys Tyr Val Leu Arg Ile Leu Gly Thr Pro Asn Pro Gln Val Trp Pro
        195                 200                 205

Glu Leu Thr Glu Leu Pro Asp Tyr Asn Lys Ile Ser Leu Lys Glu Gln
    210                 215                 220

Val Pro Met Pro Leu Glu Glu Val Leu Pro Asp Val Ser Pro Gln Ala
225                 230                 235                 240

Leu Asp Leu Leu Gly Gln Phe Leu Leu Tyr Pro Pro His Gln Arg Ile
                245                 250                 255

Ala Ala Ser Lys Ala Leu Leu His Gln Tyr Phe Thr Ala Pro Leu
            260                 265                 270

Pro Ala His Pro Ser Glu Leu Pro Ile Pro Gln Arg Leu Gly Gly Pro
        275                 280                 285

Ala Pro Lys Ala His Pro Gly Pro Pro His Ile His Asp Phe His Val
    290                 295                 300

Asp Arg Pro Leu Glu Glu Ser Leu Leu Asn Pro Glu Leu Ile Arg Pro
305                 310                 315                 320

Phe Ile Leu Glu Arg
                325
```

<210> SEQ ID NO 3
<211> LENGTH: 1053

<212> TYPE: DNA
<213> ORGANISM: Homo sapien

<400> SEQUENCE: 3

```
atggaccagt actgcatcct ggccgcatc ggggagggcg cccacggcat cgtcttcaag      60
gccaagcacg tggagactgg cgagatagtt gccctcaaga aggtggccct aaggcggttg    120
gaagacggct ccctaaccca ggccctgcgg gagattaagg ctctgcagga gatggaggac    180
aatcagtatg tggtacaact gaaggctgtg ttcccacacg gtggaggctt tgtgctggcc    240
tttgagttca tgctgtcgga tctggccgag gtggtgcgcc atgcccagag gccgctagcc    300
caggcacagg tcaagagcta cctgcagatg ctgctcaagg gtgtcgcctt ctgccatgcc    360
aacaacattg tacatcggga cctgaaacct gccaacctgc tcatcagcgc ctcaggccag    420
ctcaagatag cggactttgg cctggctcga gtctttttccc cagacggcag ccgcctctac    480
acacaccagg tggccaccag gtggtaccga gcccccgagc tcctgtatgg tgcccgccag    540
tatgaccagg gcgtcgatct gtggtctgtg ggctgcatca tggggagct gttgaatggg    600
tcccccctttt tccgggcaa gaacgatatt gaacagcttt gctatgtgct tcgcatcttg    660
ggcaccccaa accctcaagt ctggccggag ctcactgagc tgccggacta caacaagatc    720
tcctttaagg agcaggtgcc catgcccctg gaggaggtgc tgcctgacgt ctctccccag    780
gcattggatc tgctgggtca attccttctc taccctcctc accagcgcat cgcagcttcc    840
aaggctctcc tccatcagta cttcttcaca gctcccctgc ctgcccatcc atctgagctg    900
ccgattcctc agcgtctagg gggacctgcc cccaaggccc atccagggcc cccccacatc    960
catgacttcc acgtggaccg gcctcttgag gagtcgctgt tgaacccaga gctgattcgg    1020
cccttcatcc tggaggggtg aggatcctga gaa                                1053
```

<210> SEQ ID NO 4
<211> LENGTH: 346
<212> TYPE: PRT
<213> ORGANISM: Homo sapien

<400> SEQUENCE: 4

```
Met Asp Gln Tyr Cys Ile Leu Gly Arg Ile Gly Glu Gly Ala His Gly
  1               5                  10                  15
Ile Val Phe Lys Ala Lys His Val Glu Thr Gly Glu Ile Val Ala Leu
             20                  25                  30
Lys Lys Val Ala Leu Arg Arg Leu Glu Asp Gly Phe Pro Asn Gln Ala
         35                  40                  45
Leu Arg Glu Ile Lys Ala Leu Gln Glu Met Glu Asp Asn Gln Tyr Val
     50                  55                  60
Val Gln Leu Lys Ala Val Phe Pro His Gly Gly Phe Val Leu Ala
 65                  70                  75                  80
Phe Glu Phe Met Leu Ser Asp Leu Ala Glu Val Val Arg His Ala Gln
                 85                  90                  95
Arg Pro Leu Ala Gln Ala Gln Val Lys Ser Tyr Leu Gln Met Leu Leu
            100                 105                 110
Lys Gly Val Ala Phe Cys His Ala Asn Asn Ile Val His Arg Asp Leu
        115                 120                 125
Lys Pro Ala Asn Leu Leu Ile Ser Ala Ser Gly Gln Leu Lys Ile Ala
    130                 135                 140
Asp Phe Gly Leu Ala Arg Val Phe Ser Pro Asp Gly Ser Arg Leu Tyr
145                 150                 155                 160
```

```
Thr His Gln Val Ala Thr Arg Trp Tyr Arg Ala Pro Glu Leu Leu Tyr
            165                 170                 175

Gly Ala Arg Gln Tyr Asp Gln Gly Val Asp Leu Trp Ser Val Gly Cys
        180                 185                 190

Ile Met Gly Glu Leu Leu Asn Gly Ser Pro Leu Phe Pro Gly Lys Asn
    195                 200                 205

Asp Ile Glu Gln Leu Cys Tyr Val Leu Arg Ile Leu Gly Thr Pro Asn
    210                 215                 220

Pro Gln Val Trp Pro Glu Leu Thr Glu Leu Pro Asp Tyr Asn Lys Ile
225                 230                 235                 240

Ser Phe Lys Glu Gln Val Pro Met Pro Leu Glu Val Leu Pro Asp
                245                 250                 255

Val Ser Pro Gln Ala Leu Asp Leu Leu Gly Gln Phe Leu Leu Tyr Pro
            260                 265                 270

Pro His Gln Arg Ile Ala Ala Ser Lys Ala Leu Leu His Gln Tyr Phe
        275                 280                 285

Phe Thr Ala Pro Leu Pro Ala His Pro Ser Glu Leu Pro Ile Pro Gln
    290                 295                 300

Arg Leu Gly Gly Pro Ala Pro Lys Ala His Pro Gly Pro Pro His Ile
305                 310                 315                 320

His Asp Phe His Val Asp Arg Pro Leu Glu Glu Ser Leu Leu Asn Pro
                325                 330                 335

Glu Leu Ile Arg Pro Phe Ile Leu Glu Arg
            340                 345

<210> SEQ ID NO 5
<211> LENGTH: 1092
<212> TYPE: DNA
<213> ORGANISM: Homo sapien

<400> SEQUENCE: 5
atggaccagt actgcatcct gggccgcatc ggggagggcg cccacggcat cgtcttcaag      60
gccaagcacg tggagccgag ggtgggctgg cagtgtctgc cttctatcct gcagactggc     120
gagatagttg ccctcaagaa ggtggcccta aggcggttga agacggcttt ccctaaccag     180
gccctgcggg agattaaggc tctgcaggag atggaggaca tcagtatgt ggtacaactg      240 aaggctgtgt tcccacacgg tggaggcttt gtgctggcct ttgagttcat gctgtcggat     300
ctggccgagg tggtgcgcca tgcccagagg ccactagccc aggcacaggt caagagctac     360
ctgcagatgc tgctcaaggg tgtcgccttc tgccatgcca caacattgt acatcgggac     420 ctgaaacctg ccaacctgct catcagcgcc tcaggccagc tcaagatagc ggactttggc     480
ctggctcgag tcttttcccc agacggcagc cgcctctaca cacaccaggt ggccaccagg     540
tggtaccgag cccccgagct cctgtatggc gcccgccagt atgaccaggg cgtcgatctg     600
tggtctgtgg gctgcatcat gggggagctg ttgaatgggt ccccccttt cccgggcaag     660 aacgatattg aacagctttg ctatgtgctt cgcatcttgg gcaccccaaa ccctcaagtc     720
tggccggagc tcactgagct gccggactac aacaagatct cctttaagga gcaggtgccc     780
atgcccctgg aggaggtgct gcctgacgtc tctccccagg cattggatct gctgggtcaa     840
ttccttctct accctcctca ccagcgcatc gcagcttcca aggctctcct ccatcagtac     900
ttcttcacag ctcccctgcc tgcccatcca tctgagctgc cggttcctca gcgtctaggg     960
ggacctgccc caaggcccca tcagggcccc cccacatcc atgacttcca cgtggaccgg    1020
cctcttgagg agtcgctgtt gaacccagag ctgattcggc ccttcatcct ggagggtga    1080
```
ggatcctgag aa                                                    1092

<210> SEQ ID NO 6
<211> LENGTH: 359
<212> TYPE: PRT
<213> ORGANISM: Homo sapien

<400> SEQUENCE: 6

Met Asp Gln Tyr Cys Ile Leu Gly Arg Ile Gly Glu Gly Ala His Gly
 1               5                  10                  15

Ile Val Phe Lys Ala Lys His Val Glu Pro Arg Val Gly Trp Gln Cys
            20                  25                  30

Leu Pro Ser Ile Leu Gln Thr Gly Glu Ile Val Ala Leu Lys Lys Val
        35                  40                  45

Ala Leu Arg Arg Leu Glu Asp Gly Phe Pro Asn Gln Ala Leu Arg Glu
    50                  55                  60

Ile Lys Ala Leu Gln Glu Met Glu Asp Asn Gln Tyr Val Val Gln Leu
65                  70                  75                  80

Lys Ala Val Phe Pro His Gly Gly Gly Phe Val Leu Ala Phe Glu Phe
                85                  90                  95

Met Leu Ser Asp Leu Ala Glu Val Val Arg His Ala Gln Arg Pro Leu
            100                 105                 110

Ala Gln Ala Gln Val Lys Ser Tyr Leu Gln Met Leu Leu Lys Gly Val
        115                 120                 125

Ala Phe Cys His Ala Asn Asn Ile Val His Arg Asp Leu Lys Pro Ala
    130                 135                 140

Asn Leu Leu Ile Ser Ala Ser Gly Gln Leu Lys Ile Ala Asp Phe Gly
145                 150                 155                 160

Leu Ala Arg Val Phe Ser Pro Asp Gly Ser Arg Leu Tyr Thr His Gln
                165                 170                 175

Val Ala Thr Arg Trp Tyr Arg Ala Pro Glu Leu Leu Tyr Gly Ala Arg
            180                 185                 190

Gln Tyr Asp Gln Gly Val Asp Leu Trp Ser Val Gly Cys Ile Met Gly
        195                 200                 205

Glu Leu Leu Asn Gly Ser Pro Leu Phe Pro Gly Lys Asn Asp Ile Glu
    210                 215                 220

Gln Leu Cys Tyr Val Leu Arg Ile Leu Gly Thr Pro Asn Pro Gln Val
225                 230                 235                 240

Trp Pro Glu Leu Thr Glu Leu Pro Asp Tyr Asn Lys Ile Ser Phe Lys
                245                 250                 255

Glu Gln Val Pro Met Pro Leu Glu Glu Val Leu Pro Asp Val Ser Pro
            260                 265                 270

Gln Ala Leu Asp Leu Leu Gly Gln Phe Leu Leu Tyr Pro Pro His Gln
        275                 280                 285

Arg Ile Ala Ala Ser Lys Ala Leu Leu His Gln Tyr Phe Phe Thr Ala
    290                 295                 300

Pro Leu Pro Ala His Pro Ser Glu Leu Pro Val Pro Gln Arg Leu Gly
305                 310                 315                 320

Gly Pro Ala Pro Lys Ala His Pro Gly Pro Pro His Ile His Asp Phe
                325                 330                 335

His Val Asp Arg Pro Leu Glu Glu Ser Leu Leu Asn Pro Glu Leu Ile
            340                 345                 350

Arg Pro Phe Ile Leu Glu Gly
        355

<210> SEQ ID NO 7
<211> LENGTH: 1038
<212> TYPE: DNA
<213> ORGANISM: Homo sapien

<400> SEQUENCE: 7

```
atggaccagt actgcatcct gggccgcatc ggggagggcg cccacggcat cgtcttcaag      60
gccaagcacg tggagccgag ggtgggctgg cagtgtctgc cttctatcct gcagactggc     120
gagatagttg ccctcaagaa ggtggcccta aggcggttgg aggacggctt ccctaaccag     180
gccctgcggg agattaaggc tctgcaggag atggaggaca atcagtatgt ggtacaactg     240
aaggctgtgt tcccacacgg tggaggcttt gtgctggcct ttgagttcat gctgtcggat     300
ctggccgagg tggtgcgcca tgcccagagg ccactagccc aggcacaggt caagagctac     360
ctgcagatgc tgctcaaggg tgtcgccttc tgccatgcca acaacattgt acatcgggac     420
ctgaaacctg ccaacctgct catcagcgcc tcaggccagc tcaagatagc ggactttggc     480
ctggctcgag tcttttcccc agacggcagc cgcctctaca cacaccaggt ggccaccagg     540
tggtaccgag cccccgagct cctgtatggt gcccgccagt atgaccaggg cgtcgatctg     600
tggtctgtgg gctgcatcat gggggagctg ttgaatgggt ccccccttt tccgggcaag     660
aacgatattg aacagctttg ctatgtgctt cgcatcttgg gcacccccaa ccctcaagtc     720
tggccggagc aggtgcccat gcccctggag gaggtgctgc ctgacgtctc tccccaggca     780
ttggatctgc tgggtcaatt ccttctctac cctcctcacc agcgcatcgc agcttccaag     840
gctctcctcc atcagtactt cttcacagct cccctgcctg ccatccatc tgagctgccg      900
attcctcagc gtctaggggg acctgccccc aaggcccatc cagggccccc ccacatccat     960
gacttccacg tggaccggcc tcttgaggag tcgctgttga acccagagct gattcggccc    1020
ttcatcctgg aggggtga                                                   1038
```

<210> SEQ ID NO 8
<211> LENGTH: 345
<212> TYPE: PRT
<213> ORGANISM: Homo sapien

<400> SEQUENCE: 8

```
Met Asp Gln Tyr Cys Ile Leu Gly Arg Ile Gly Glu Gly Ala His Gly
  1               5                  10                  15

Ile Val Phe Lys Ala Lys His Val Glu Pro Arg Val Gly Trp Gln Cys
             20                  25                  30

Leu Pro Ser Ile Leu Gln Thr Gly Glu Ile Val Ala Leu Lys Lys Val
         35                  40                  45

Ala Leu Arg Arg Leu Glu Asp Gly Phe Pro Asn Gln Ala Leu Arg Glu
     50                  55                  60

Ile Lys Ala Leu Gln Glu Met Glu Asp Asn Gln Tyr Val Val Gln Leu
 65                  70                  75                  80

Lys Ala Val Phe Pro His Gly Gly Gly Phe Val Leu Ala Phe Glu Phe
                 85                  90                  95

Met Leu Ser Asp Leu Ala Glu Val Val Arg His Ala Gln Arg Pro Leu
            100                 105                 110

Ala Gln Ala Gln Val Lys Ser Tyr Leu Gln Met Leu Leu Lys Gly Val
        115                 120                 125

Ala Phe Cys His Ala Asn Asn Ile Val His Arg Asp Leu Lys Pro Ala
    130                 135                 140
```

```
Asn Leu Leu Ile Ser Ala Ser Gly Gln Leu Lys Ile Ala Asp Phe Gly
145                 150                 155                 160

Leu Ala Arg Val Phe Ser Pro Asp Gly Ser Arg Leu Tyr Thr His Gln
                165                 170                 175

Val Ala Thr Arg Trp Tyr Arg Ala Pro Glu Leu Leu Tyr Gly Ala Arg
            180                 185                 190

Gln Tyr Asp Gln Gly Val Asp Leu Trp Ser Val Gly Cys Ile Met Gly
        195                 200                 205

Glu Leu Leu Asn Gly Ser Pro Leu Phe Pro Gly Lys Asn Asp Ile Glu
    210                 215                 220

Gln Leu Cys Tyr Val Leu Arg Ile Leu Gly Thr Pro Asn Pro Gln Val
225                 230                 235                 240

Trp Pro Glu Gln Val Pro Met Pro Leu Glu Val Leu Pro Asp Val
                245                 250                 255

Ser Pro Gln Ala Leu Asp Leu Leu Gly Gln Phe Leu Leu Tyr Pro Pro
                260                 265                 270

His Gln Arg Ile Ala Ala Ser Lys Ala Leu Leu His Gln Tyr Phe Phe
            275                 280                 285

Thr Ala Pro Leu Pro Ala His Pro Ser Glu Leu Pro Ile Pro Gln Arg
        290                 295                 300

Leu Gly Gly Pro Ala Pro Lys Ala His Pro Gly Pro Pro His Ile His
305                 310                 315                 320

Asp Phe His Val Asp Arg Pro Leu Glu Glu Ser Leu Leu Asn Pro Glu
                325                 330                 335

Leu Ile Arg Pro Phe Ile Leu Glu Gly
            340                 345

<210> SEQ ID NO 9
<211> LENGTH: 7
<212> TYPE: PRT
<213> ORGANISM: Unknown
<220> FEATURE:
<223> OTHER INFORMATION: Sequence which characterizes the cyclin binding
      domain of cyclin-dependant kinases.

<400> SEQUENCE: 9

Pro Asn Gln Ala Leu Arg Glu
 1               5

<210> SEQ ID NO 10
<211> LENGTH: 7
<212> TYPE: PRT
<213> ORGANISM: Unknown
<220> FEATURE:
<223> OTHER INFORMATION: Sequence which characterizes the cyclin binding
      domain of cyclin-dependant kinases.

<400> SEQUENCE: 10

Pro Phe Thr Ala Ile Arg Glu
 1               5

<210> SEQ ID NO 11
<211> LENGTH: 7
<212> TYPE: PRT
<213> ORGANISM: Unknown
<220> FEATURE:
<223> OTHER INFORMATION: Sequence which characterizes the cyclin binding
      domain of cyclin-dependant kinases.

<400> SEQUENCE: 11
```

```
Pro Ile Ser Ser Leu Arg Glu
 1               5

<210> SEQ ID NO 12
<211> LENGTH: 7
<212> TYPE: PRT
<213> ORGANISM: Unknown
<220> FEATURE:
<223> OTHER INFORMATION: Sequence which characterizes the cyclin binding
      domain of cyclin-dependant kinases.

<400> SEQUENCE: 12

Pro Ile Thr Ala Leu Arg Glu
 1               5

<210> SEQ ID NO 13
<211> LENGTH: 7
<212> TYPE: PRT
<213> ORGANISM: Unknown
<220> FEATURE:
<223> OTHER INFORMATION: Sequence which characterizes the cyclin binding
      domain of cyclin-dependant kinases.

<400> SEQUENCE: 13

Pro Leu Ser Thr Ile Arg Glu
 1               5

<210> SEQ ID NO 14
<211> LENGTH: 7
<212> TYPE: PRT
<213> ORGANISM: Unknown
<220> FEATURE:
<223> OTHER INFORMATION: Sequence which characterizes the cyclin binding
      domain of cyclin-dependant kinases.

<400> SEQUENCE: 14

Pro Ile Ser Thr Val Arg Glu
 1               5

<210> SEQ ID NO 15
<211> LENGTH: 7
<212> TYPE: PRT
<213> ORGANISM: Unknown
<220> FEATURE:
<223> OTHER INFORMATION: Sequence which characterizes the cyclin binding
      domain of cyclin-dependant kinases.

<400> SEQUENCE: 15

Pro Ser Thr Ala Ile Arg Glu
 1               5

<210> SEQ ID NO 16
<211> LENGTH: 7
<212> TYPE: PRT
<213> ORGANISM: Unknown
<220> FEATURE:
<223> OTHER INFORMATION: Sequence which characterizes the cyclin binding
      domain of cyclin-dependant kinases.

<400> SEQUENCE: 16

Asn Arg Thr Ala Leu Arg Glu
 1               5

<210> SEQ ID NO 17
<211> LENGTH: 21
<212> TYPE: PRT
<213> ORGANISM: Homo spaien
```

-continued

```
<400> SEQUENCE: 17

His Asp Phe His Val Asp Arg Pro Leu Glu Glu Ser Leu Ile Asn Pro
1               5                   10                  15

Glu Leu Ile Arg Pro
            20
```